US010156573B2

(12) United States Patent
Tian et al.

(10) Patent No.: US 10,156,573 B2
(45) Date of Patent: Dec. 18, 2018

(54) TRI-COLOR DUAL GLUCOSE AND OXYGEN SENSORS AND METHODS OF PREPARING AND USING THEM

(71) Applicant: Arizona Board of Regents, a body corporate of the State of Arizona, acting for and on behalf of Arizona State, Scottsdale, AZ (US)

(72) Inventors: Yanqing Tian, Tempe, AZ (US); Liqiang Zhang, Chandler, AZ (US); Fengyu Su, Tempe, AZ (US); Deirdre Meldrum, Phoenix, AZ (US); Sean Buizer, Tempe, AZ (US)

(73) Assignee: Arizona Board of Regents, a body corporate of the State of Arizona, acting for and on behalf of Arizona State University, Scottsdale, AZ (US)

( * ) Notice: Subject to any disclaimer, the term of this patent is extended or adjusted under 35 U.S.C. 154(b) by 1140 days.

(21) Appl. No.: 14/210,357

(22) Filed: Mar. 13, 2014

(65) Prior Publication Data

US 2014/0273043 A1    Sep. 18, 2014

Related U.S. Application Data

(60) Provisional application No. 61/786,046, filed on Mar. 14, 2013.

(51) Int. Cl.
| | |
|---|---|
| G01N 33/66 | (2006.01) |
| G01N 21/64 | (2006.01) |
| G01N 33/58 | (2006.01) |
| C12Q 1/54 | (2006.01) |

(52) U.S. Cl.
CPC ......... *G01N 33/66* (2013.01); *G01N 21/6486* (2013.01); *G01N 33/582* (2013.01); *C12Q 1/54* (2013.01); *Y10T 436/144444* (2015.01); *Y10T 436/207497* (2015.01)

(58) Field of Classification Search
CPC combination set(s) only.
See application file for complete search history.

(56) References Cited

U.S. PATENT DOCUMENTS 6,366,793 B1 *  4/2002  Bell ................. G01N 33/66
                                                      422/68.1
7,388,110 B2 *  6/2008  Ochiai ................ C07F 5/025
                                                      562/7

OTHER PUBLICATIONS

S. Manju, K. Sreenivasan, "Detection of glucose in synthetic tear fluid using dually functionalized gold nanoparticles," Talanta vol. 85, Issue 5, Oct. 15, 2011, pp. 2643-2649.*

(Continued)

*Primary Examiner* — Christopher Adam Hixson
*Assistant Examiner* — Michelle Adams
(74) *Attorney, Agent, or Firm* — Byrne Poh LLP; Nina R. Horan

(57) ABSTRACT

The present disclosure relates to an optical fluorescence sensor comprising a probe for sensing glucose, an intra-reference probe, and a matrix. The present disclosure also relates to an optical fluorescence dual sensor comprising a probe for sensing glucose having two boronic acid moieties, a probe for sensing oxygen comprising modified porphyrin, an intra-reference probe that is rhodamine-based, and a matrix. The present disclosure additionally relates to methods of preparing these sensors and methods of using them.

25 Claims, 10 Drawing Sheets

(56) References Cited

OTHER PUBLICATIONS

David B. Cordes and Bakthan Singaram, "A unique, two-component sensing system for fluorescence detection of glucose and other carbohydrates," Pure Appl. Chem., vol. 84, No. 11, pp. 2183-2202 (2012).*
Best, Q.A., et al., "Design and Investigation of a Series of Rhodamine-based Fluorescent Probes for Optical Measurements of pH", In Organic Letters, vol. 12, No. 14, Jul. 2010, pp. 3219-3221.
Blaker, G.J., et al., "The Glucose, Insulin and Glutamine Requirements of Suspension Cultures of HeLa Cells in a Defined Culture Medium", In Journal of Cell Science, vol. 9, Sep. 1971, pp. 529-537.
Brauer, H.A., et al., "Impact of Tumor Microenvironment and Epithelial Phenotypes on Metabolism in Breast Cancer", In Clinical Cancer Research, vol. 19, No. 3, Feb. 2013, pp. 571-585.
Briczinski E.P., et al., "Transport of Glucose by Bifidobacterium Animalis Subsp. *Lactis* Occurs via Facilitated Diffusion", In Applied Environmental Microbiology, vol. 74, No. 22, Nov. 2008, pp. 6941-6948.
Chen, B.K., et al., "Temperature Responsive Methacrylamide Polymers with Antibacterial Activity", In Chinese Journal of Polymer Science, vol. 28, No. 4, Apr. 2010, pp. 607-613.
Chen, R., et al., "Comparative Studies of *Escherichia coli* Strains Using Different Glucose Uptake Systems: Metabolism and Energetics", In Biotechnology and Bioengineering, vol. 56, No. 5, Dec. 1997, pp. 583-590.
Daly, M.E., et al., "Acute Effects on Insulin Sensitivity and Diurnal Metabolic Profiles of a High-sucrose Compared with a High-starch Diet", In America Journal of Clinical Nutrition, vol. 67, Jun. 1998, pp. 1186-1196.
Deberardinis, R.J., et al., "Cellular Metabolism and Disease: What do Metabolic Outliers Teach Us?", In Cell, vol. 148, No. 6, Mar. 2012, pp. 1132-1144.
Denkert, C., et al., "Mass Spectrometry-based Metabolic Profiling Reveals Different Metabolites Patterns in Invasive Ovarian Carcinomas and Ovarian Borderline Tumors", In Cancer Research, vol. 66, No. 22, Nov. 2006, pp. 10795-10804.
Fang, H., et al., "Progress in Boronic Acid-based Fluorescent Glucose Sensors", In Journal of Fluorescence, vol. 14, No. 5, Sep. 2004, pp. 481-489.
Fornasiero F., et al., "Steady-state Diffusion of Water Through Soft-contact-lens Materials", In Biomaterials, vol. 26, Oct. 2005, pp. 5704-5716.
Fowler, J.S., and Ido, T., "Initial and Subsequent Approach for the Synthesis of 18FDG", In Seminars in Nuclear Medicine, vol. 32, No. 1, Jan. 2002, pp. 6-12.
Gatenby, R.A., and Gillies, R.J., "Why do Cancers have High Aerobic Glycolysis?", In Nature Reviews Cancer, vol. 4, Nov. 2004, pp. 891-899.
Glunde, K., et al., "Magnetic Resonance Spectroscopy in Metabolic and Molecular Imaging, and Diagnosis of Cancer", In Chemical Reviews, vol. 110, No. 5, May 2010, pp. 3043-3059.
Griffin, J.L. and Shockcor, J.P., "Metabolic Profiles of Cancer Cells", In Nature Reviews Cancer, vol. 4, Jul. 2004, pp. 551-561.
Guo, P., et al., "Domain II Plays a Crucial Role in the Function of Ribosome Recycling Factor", In Biochemical Journal, Feb. 2006, vol. 393, pp. 767-777.
Haas, M., et al., "YkrB is the Main Peptide Deformylase in Bacillus Subtilis, a Eubacterium Containing Two Functional Peptide Deformylases", In Microbiology, vol. 147, Jul. 2001, pp. 1783-1791.
Heller, A., "Implanted Electrochemical Glucose Sensors for the Management of Diabetes", In Annual Review of Biomedical Engineering, vol. 1, Aug. 1999, pp. 153-175.
Heller, A., and Feldman, B., "Electrochemical Glucose Sensors and their Applications in Diabetes Management", In Chemical Reviews, vol. 108, Jul. 2008, pp. 2482-2505.
Heo, Y.J., et al., "Long-term in Vivo Glucose Monitoring Using Fluorescent Hydrogel Fibers", In Proceedings of the National Academy of Science, USA, Aug. 2011, vol. 108, No. 33, pp. 13399-13403.
Huang, E.S., et al., "Projecting the Future Diabetes Population Size and Related Costs for the US", In Diabetes Care, vol. 32, No. 12, Dec. 2009, pp. 2225-2229.
James, T.D., et al., "Novel Saccharide-photoinduced Electron Transfer Sensors based on the Interaction of Boronic Acid and Amine", In Journal of the American Chemical Society, vol. 117, Sep. 1995, pp. 898289-898297.
Jelenc, P.C., "Rapid Purification of Highly Active Ribosomes from *Escherichia coli*", In Analytical Biochemistry, vol. 105, No. 1, Jun. 1980, pp. 369-374.
Kaelin, W.G. and Thompson, C.B., "Q&A: Cancer: Clues from Cell Metabolism", In Nature, vol. 465, Jun. 2010, pp. 562-564.
Kawanishi T., et al., "A Study of Boronic Acid Based Fluorescent Glucose Sensors", In Journal of Fluorescence, vol. 14, No. 5, Sep. 2004, pp. 499-512.
Kermis, H.R., et al., "Dual Excitation Ratiometric Fluorescent pH Sensor for Noninvasive Bioprocess Monitoring: Development and Application", In Biotechnology Progress, vol. 18, Sep. 2002, pp. 1047-1053.
Li, L., and Walt, D.R., "Dual Analyte Fiberloptic Sensor for the Siumultaneous and Continuous Measurement of Glucose and Oxygen", In Analytical Chemistry, Oct. 1995, vol. 67, No. 20, pp. 3746-3752.
Li, S., et al., "Development of Boronic Acid Grafted Random Copolymer Sensing Fluid for Continuous Glucose Monitoring", In Biomacromolecules, vol. 10, No. 1, Dec. 2009, pp. 113-118.
Lorand, J.P., and Edwards, J.O., "Polyol Complexes and Structure of the Benzeneboronate Ion", In Journal of Organic Chemistry, vol. 24, Jun. 1959, pp. 769-774.
Lu, H., et al., "New Ratiometric Optical Oxygen and pH Dual Sensors with Three Emission Colors for Measuring Photosynthetic Activity in Cyanobacteria", In Journal of Materials Chemistry, vol. 48, Jan. 2011, pp. 19293-19301.
Mader, H.S., and Wolfbeis, O.S., "Boronic Acid Based Probes for Microdetermination of Saccharides and Glycosylated Biomolecules", In Microchimica Acta, vol. 162, Mar. 2008, pp. 1-34.
McKean, B.D. and Gough, D.A., "A Telemetry-instrumentation System for Chronically Implanted Glucose and Oxygen Sensors", In IEEE Transactions on Biomedical Engineering, vol. 35, No. 7, Jul. 1988, pp. 526-532.
Monod, J., "The Growth of Bacterial Cultures", In Annual Review of Microbiology, vol. 3, Oct. 1949, pp. 371-394.
Munoz-Pinedo, C., et al., "Cancer Metabolism: Current Perspectives and Future Directions", Cell Death and Disease, vol. 3, Jan. 2012, article e248, pp. 1-10.
Natarajan, A. and Srienc, F., "Glucose Uptake Rates of Single *E. coli* Cells Grown in Glucose-limited Chemostat Cultures", In Journal of Microbiological Methods, Sep. 2000, vol. 42, pp. 87-96.
Pickup, J.C., et al., "Fluorescence-based Glucose Sensors", In Biosensors and Bioelectronics, Jun. 2005, vol. 20, pp. 2555-2656.
Pringsheim, E., et al., "A Polyaniline with Near-infrared Optical Response to Saccharide", In Advanced Materials, vol. 11, No. 10, Jul. 1999, pp. 865-868.
Pritchard, K.I., et al., "Prospective Study of 2-[18F]fluorodeoxyglucose Positron Emission Tomography in the Assessment of Regional Nodal Spread of Disease in Patients with Breast Cancer: an Ontario Clinical Oncology Group Study", In Journal of Clinical Oncology, vol. 30, No. 12, Apr. 2012, pp. 1274-1249.
Ramirez-Peinado, S., et al., "2-deoxyglucose Induces Noxa-dependent Apoptosis in Alveolar Rhabdomyosarcoma", In Cancer Research, vol. 71, No. 21, Nov. 2011, pp. 6796-6806.
Roupe, K.A., et al., "Preparative Enzymatic Synthesis and HPLC Analysis of Rhapontigenin: Application to Metabolism, Pharmacokinetics and Anti-cancer Studies," Journal of Pharmacy and Pharmaceutical Sciences, vol. 8, No. 3, Aug. 2005, pp. 374-386.
Schaeferling, M. and Duerkop, A., "Intrinsically Referenced Fluorimetric Sensing and Detecting Schemes: Methods, Advantages and Applications", Springer Series on Fluorescence, vol. 5, Mar. 2008, pp. 373-414.

(56) References Cited

OTHER PUBLICATIONS

Shibata, H., et al., "Injectable Hydrogel Microbeads for Fluorescence-based in Vivo Continuous Glucose Monitoring", In Proceedings of the National Academy of Sciences, vol. 107, No. 42, Oct. 2010, pp. 17894-17898.

Steiner, M.S., et al., "Optical Methods for Sensing Glucose", In Chemical Society Reviews, vol. 40, Jun. 2011, pp. 4805-4839.

Teusink, B., et al., "Intracellular Glucose Concentration in Depressed Yeast Cells Consuming Glucose is High Enough to Reduce the Glucose Transport Rate by 50%", In Journal of Bacteriology, vol. 180, No. 3, Feb. 1998, pp. 556-562.

Tian, Y., et al., "A new Cross-linkable Oxygen Sensor Covalently Bonded into Poly(2-hydroxyethyl methacrylate)-co-polyacrylamide Thin Film for Dissolved Oxygen Sensing", In Chemistry of Materials, Feb. 2010, vol. 22, No. 6, pp. 2069-2078.

Tian, Y., et al., "A Series of Naphthalimide Derivatives as Intra and Extracellular pH Sensors", In Biomaterials, vol. 31, No. 29, Oct. 2010, pp. 7400-7422.

Tian, Y., et al., "Dual Fluorescent Sensing of pH and Dissolved Oxygen using a Membrane Made from Polymerizable Sensing Monomers", In Sensors and Actuators B: Chemical, Jun. 2010, vol. 147, No. 2, pp. 714-722.

Tian, Y., et al., "Influence of Matrices on Oxygen Sensing of Three Sensing Films with Chemically Conjugated Platinum Porphyrin Probes and Preliminary Application for Monitoring of Oxygen Consumption of *Escherichia coli* (*E. coli*)", In Sensors and Actuators B: Chemical, Oct. 2010, vol. 150, No. 2, pp. 579-587.

Vander Heiden, M.G., et al., "Growth Factors can Influence Cell Growth and Survival through Effects on Glucose Metabolism", Molecular and Cellular Biology, Sep. 2001, vol. 21, No. 17, pp. 5899-5912.

Vander Heiden, M.G., et al., "Understanding the Warburg Effect: the Metabolic Requirements of Cell Proliferation", In Science, May 2009, vol. 324, No. 5930, pp. 1029-1033.

Wang, J., "Glucose Biosensors: 40 Years of Advances and Challenges", In Electroanalysis, vol. 13, No. 12, Aug. 2001, pp. 983-988.

Wang, Y., et al., "Influence of Water States in Hydrogels on the Transmissibility and Permeability of Oxygen in Contact Lens Materials", In Applied Surface Science, vol. 255, Nov. 2008, pp. 604-606.

Wu, Q., et al., "Organization of Glucose-responsive Systems and their Properties", In Chemical Reviews, vol. 111, No. 12, Sep. 2011, pp. 7855-7875.

Xu, H., et al., "A Real-time Ratiometric Method for the Determination of Molecular Oxygen Inside Living Cells using Sol-gel-based Spherical Optical Nanosensors with Applications to Rat C6 Glioma", In Analytical Chemistry, vol. 73, No. 17, Sep. 2001, pp. 4124-4133.

Yoshioka, K., et al., "A Novel Fluorescent Derivative of Glucose Applicable to the Assessment of Glucose Uptake Activity of *Escherichia coli*", In Biochimica et Biophysica Acta, vol. 1289, Feb. 1996, pp. 5-9.

Zhou, X., et al., "An Fret-based Ratiometric Chemosensor for in Vitro Cellular Fluorescence Analyses of pH", In Biomaterials, Jan. 2012, vol. 33, No. 1, pp. 171-180.

\* cited by examiner

TRI-COLOR DUAL GLUCOSE AND OXYGEN SENSORS AND METHODS OF PREPARING AND USING THEM

This application claims the benefit U.S. Provisional Application No. 61/786,046, filed Mar. 14, 2013, which is incorporated by reference herein in its entirety.

FEDERALLY SPONSORED RESEARCH OR DEVELOPMENT

This invention was made with government support under CA 164250 and HG002360 awarded by the National Institutes of Health. The government has certain rights in the invention.

FIELD OF THE INVENTION

The present disclosure relates to an optical fluorescence sensor comprising a probe for sensing glucose, an intra-reference probe, and a matrix. The present disclosure also relates to an optical fluorescence dual sensor comprising a probe for sensing glucose, a probe for sensing oxygen, an intra-reference probe, and a matrix. The present disclosure additionally relates to methods of preparing these sensors and methods of using them.

BACKGROUND OF THE INVENTION

Glucose metabolism not only is the main energy source for cells, but also provides essential biomass for proliferating cells, including cancer cells [1]. Many diseases are associated with glucose transport and metabolic disorders, such as myocardial ischemia, type 2 diabetes and cancer [2]. In proliferating cells, especially cancer cells, the glucose metabolism is reprogrammed (Warburg Effect) to cater for unconstrained proliferation and invasion [1, 3-5]. Therefore, monitoring glucose metabolism of cells can provide important information that reflects a cell response to stimuli and proliferative states, which are extremely useful in cancer therapeutic diagnoses, in wound healing diagnoses and for fundamental understating of biological processes of the metabolism.

Glucose metabolism is composed of hundreds of reactions and metabolites; however, it can be simplified as below:

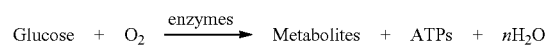

Focusing on these metabolites and enzymes, many assay kits and techniques have been developed to detect the metabolic changes that occur in cells, tissues or living bodies [6]. Some traditional assay techniques have also been applied to the detection of metabolic changes, such as high-performance liquid chromatography (HPLC), mass spectrometry (MS) and NMR spectroscopy [7-10]. For measuring glucose uptake, one available method is the radiometric assay, which is based on radiolabeled ($^3$H, $^{14}$C) glucose [11, 12]. Due to the rapid metabolism of glucose in cells, the assay should be finished in a short time to avoid transporting the radiolabeled final products ($H_2O$ and $CO_2$) out of cells. Therefore, researchers now prefer to use non-metabolizable analogs of glucose, such as 3-o-methylglucose, 2-deoxyglucose (2-DG), fluoro-deoxyglucose ($^{18}$F-FDG) and 2-(N-(7-nitrobenz-2-oxa-1,3-diazol-4-yl)amino)-2-deoxyglucose (2-NBDG) [2, 14-16]. These nonmetabolizable analogs of glucose will form metabolic stress in the cells, which will induce cell death [17]. None of these methods provide a real-time direct assay for glucose metabolism in living cells or organisms.

Innumerable glucose sensors and devices have been developed by researchers in this field, including electrochemical glucose sensors [18], optical (fluorescence and absorbance) glucose sensors [19, 20] and glucose selective polymeric sensing fluid based on direct binding [21]. According to the method for recognition of glucose, Steiner et al. classified these sensors into five fundamental types [22]: type I based on the specific binding of glucose to enzymes/coenzymes, type it based on the detection of glucose metabolites produced by certain enzymes, type III based on the interaction between glucose and organic boronic acids, type IV based on concanavalin A (Con A) and type V based on other glucose binding proteins. Organic boronic acids can interact with 1,2- or 1,3-diols to form a complex of five or six membered cyclic esters in aqueous solution [22-27]. The interaction is reversible, which is ideal to "true sensor" design [22]. The reversible complexation is required for a sensor that can monitor the continuous change of target molecules. Shinkai and his colleagues developed organic boronic acids by a modification of anthracene with a bis-phenylboronic acid (GS-COOH, FIG. 1) and its derivatives, which possess photo-induced electron transfer (PET) effect [25, 26]. Because of the unique cleft-like structure, the compound GS and its related hydrogels showed high selectivity and sensitivity to glucose [25, 28, 29].

SUMMARY OF THE INVENTION

The present disclosure provides an optical fluorescence sensor having two emission colors. In particular, the optical fluorescence sensors comprise a probe for sensing glucose, an intra-reference probe and a matrix.

The probe for sensing glucose has formula I:

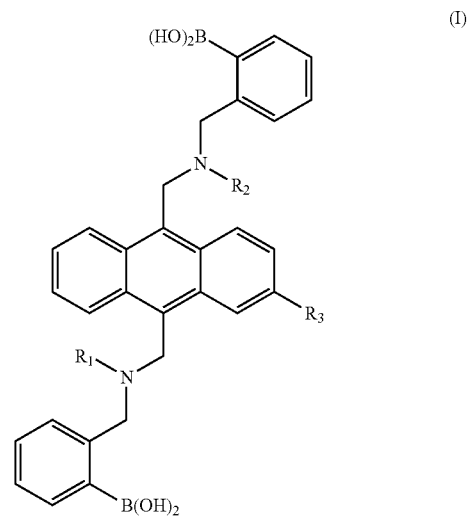

wherein $R_1$ and $R_2$ can be the same or different and are $C_nH_{2n+1}$, where n is an integer selected from the group consisting of 0, 1, 2, 3, 4, 5, 6, 7 and 8;

$R_3$ is selected from the group consisting of $(CH_2)_mC(O)OH$, $O(CH_2)_mC(O)OH$, $NH(CH_2)_mC(O)OH$, $(CH_2)_mC(O)OR_4$, $O(CH_2)_mC(O)OR_4$, $NH(CH_2)_mC(O)OR_4$, $(CH_2)_mC(O)NH(CH_2)_m NH-A$, $O(CH_2)_mC(O)NH(CH_2)_m NH-A$, $NH(CH_2)_mC(O)NH(CH_2)_m NH-A$, $(CH_2)_mC(O)O(CH_2)_m NH-A$, $O(CH_2)_mC(O)O(CH_2)_m NH-A$, $NH(CH_2)_mC(O)O(CH_2)_m NH-A$, $(CH_2)_mC(O)NH(CH_2)_m NH-M'A$, $O(CH_2)_mC(O)NH(CH_2)_m NH-M'A$, $NH(CH_2)_mC(O)NH(CH_2)_m NH-M'A$, $(CH_2)_mC(O)O(CH_2)_m NH-M'A$, $O(CH_2)C(O)O(CH_2)_m NH-M'A$, $NH(CH_2)_mC(O)O(CH_2)NH-M'A$, $(CH_2)_mC(O)NH(CH_2)_m NH-VA$, $O(CH_2)_mC(O)NH(CH_2)_m NH-VA$, $NH(CH_2)_mC(O)NH(CH_2)_m NH-VA$, $(CH_2)_mC(O)O(CH_2)_m NH-VA$, $O(CH_2)_mC(O)O(CH_2)_m NH-VA$, $NH(CH_2)_mC(O)O(CH_2)_m NH-VA$;

m is an integer selected from the group of consisting of 0, 1, 2, 3, 4, 5, 6, 7, 8, 9, 10, 11 and 12;

$R_4$ is an activating group.

M'A is

A is

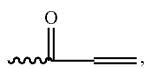

and VA is

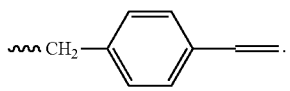

In some embodiments, the probe for sensing glucose is:

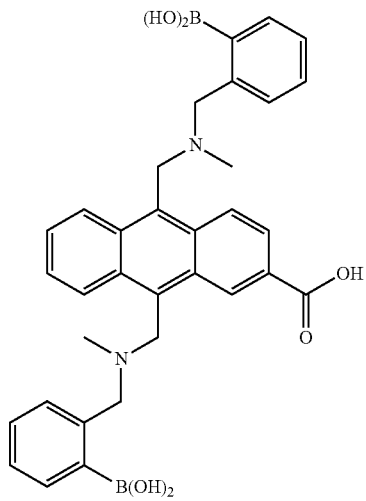 [SMILES: CN(Cc1ccccc1B(O)O)Cc1c2ccccc2c(CN(C)Cc2ccccc2B(O)O)c2cc(C(=O)O)ccc12]

or an activated ester thereof.

The intra-reference probe has formula III:

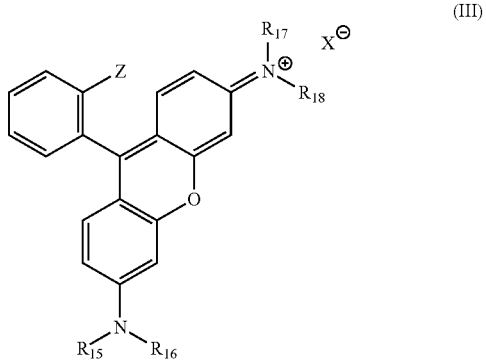

wherein $R_{15}$, $R_{16}$, $R_{17}$, and $R_{18}$ can be the same or different and are $C_nH_{2n+1}$, where n is an integer selected from the group consisting of 1, 2, 3, 4, 5, 6, 7 and 8;

X is an anion; and

Z is selected from the group consisting of: $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, $CH_2(OCH_2CH_2)_rOVA$.

r is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

In some embodiments, the intra-reference probe is:

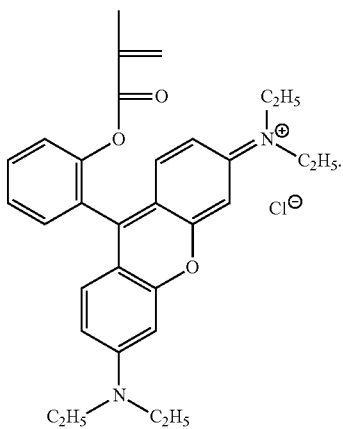 [SMILES: C=C(C)C(=O)Oc1ccccc1-c1c2ccc(=[N+](CC)CC)cc-2oc2cc(N(CC)CC)ccc12 ; [Cl-]]

The matrix comprises a polymer selected from the group consisting of acrylamide, N-(6-aminohexyl)methacrylamide, and poly(ethylene glycol) dimethacrylate, methoxypoly(ethylene glycol) methacrylate, 2-hydroxyethyl methacrylate and combinations thereof.

The present disclosure also provides an optical fluorescence dual sensor having three emission colors. In particular, the optical fluorescence sensors comprise a probe for sensing glucose, a probe for sensing oxygen, an intra-reference probe and a matrix.

The probe for sensing glucose, the intra-reference probe and the matrix are as defined above.

The probe for sensing oxygen has formula II:

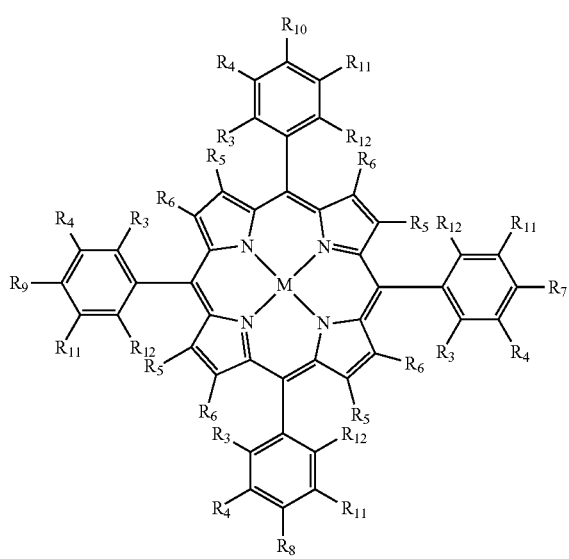

(II)

where
M is selected from Pt or Pd;
$R_{11}$ and $R_{12}$ can be the same or different and are independently selected from the group consisting of H, F, Cl, Br, I, $CH_3$, $OCH_3$ and $OC_2H_5$;
$R_3$ and $R_4$ can be the same or different and are independently selected from the group consisting of H, F, Cl, Br, I, $CH_3$, $OCH_3$ and $OC_2H_5$;
$R_5$ and $R_6$ can be the same or different and are independently selected from the group consisting of H, F, Cl, Br, I, $CH_3$, $OCH_3$ and $OC_2H_5$;
$R_7$, $R_8$, $R_9$ and $R_{10}$ can be the same or different and are independently selected from the group consisting of $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, where
M'A is

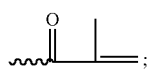;

A is

;

VA is

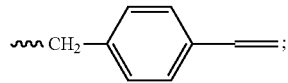;

p is an integer selected from the group of consisting of 2, 3, 4, 5, 6, 7, 8, 9, 10, 11 and 12; and q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41.42, 43, 44, 140, 141, 142, 143, 144, 145, 146, 147, 148, 149 and 150.

In some embodiments, the probe for sensing oxygen is:

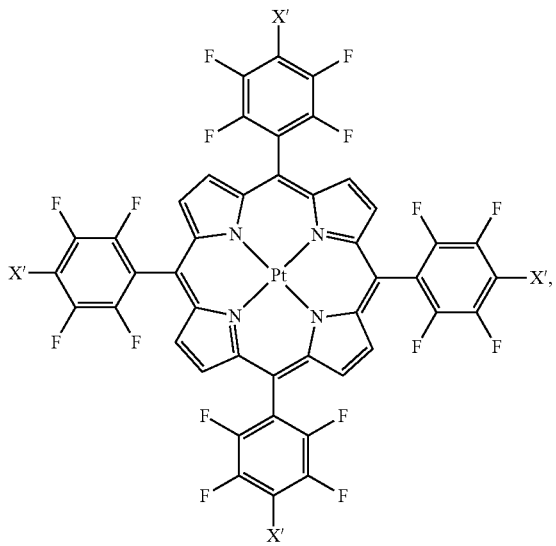

wherein X' is

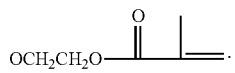.

The present disclosure also provides a method of preparing an optical fluorescence sensor. In the first step, an intra-reference probe is copolymerized with 2-hydroxyethyl methacrylate, N-(6-aminohexyl)methacrylamide, and acrylamide onto a substrate. The substrate is preferably trimethylsilylpropyl acrylate modified PET, glass, or quartz glass. In some embodiments, the substrate is quart glass.

The intra-reference probe has formula (II) as defined above. In some embodiments, the intra-reference probe is:

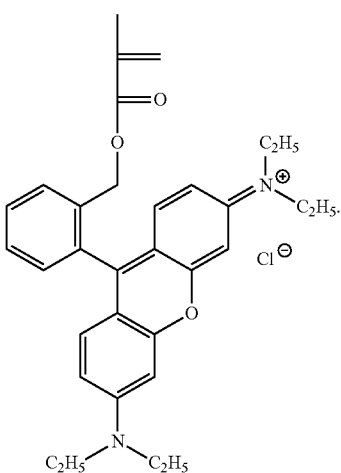 [SMILES: C=C(C)C(=O)OCc1ccccc1-c1c2ccc(=[N+](CC)CC)cc-2oc2cc(N(CC)CC)ccc12 ; [Cl-]]

In some embodiments, copolymerizing the intra-reference probe, with 2-hydroxyethyl methacrylate, N-(6-aminohexyl)methacrylamide, and acrylamide forms poly(2-hydroxyethyl methacrylate), poly(N-(6-aminohexyl)methacrylamide), poly(acrylamide), poly(2-hydroxyethyl methacrylate)-co-polyacrylamide-co-poly(N-(6-aminohexyl)methacrylamide) and their composites with the polymerized probe.

In the second step, a probe for sensing glucose is attached or immobilized onto the substrate. The probe for sensing glucose is as defined above. In some embodiments, the probe for sensing glucose is:

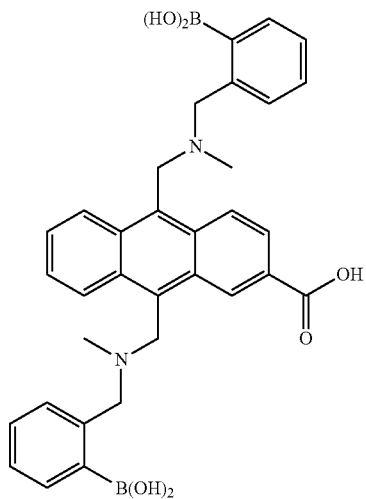 [SMILES: CN(Cc1ccccc1B(O)O)Cc1c2ccccc2c(CN(C)Cc2ccccc2B(O)O)c2cc(C(=O)O)ccc12]

or an activated ester thereof.

In alternate embodiments, the method of preparing an optical fluorescence sensor comprises the step of copolymerizing a probe for sensing glucose and an intra-reference probe, with 2-hydroxyethyl methacrylate, N-(6-aminohexyl)methacrylamide, and acrylamide onto a substrate. The probe for sensing glucose has formula (I) as defined above and the intra-reference probe has formula (III) as defined above.

In some embodiments, copolymerizing the probe for sensing glucose and the intra-reference probe, with 2-hydroxyethyl methacrylate, N-(6-aminohexyl)methacrylamide, and acrylamide forms poly(2-hydroxyethyl methacrylate), poly(N-(6-aminohexyl)methacrylamide), poly(acrylamide), poly(2-hydroxyethyl methacrylate)-co-polyacrylamide-co-poly(N-(6-aminohexyl)methacrylamide) and their composites with the polymerized probes.

The present invention also provides a method of preparing an optical fluorescence dual sensor. In the first step of the method, a probe for sensing oxygen, and an intra-reference probe are copolymerized with poly(2-hydroxyethyl methacrylate), polyacrylamide, and poly(2-hydroxyethyl methacrylate)-co-polyacrylamide onto a substrate. The substrate is as defined above. In some embodiments, the substrate is quartz glass.

The probe for sensing oxygen has formula II as defined above. In some embodiments, the probe for sensing oxygen is:

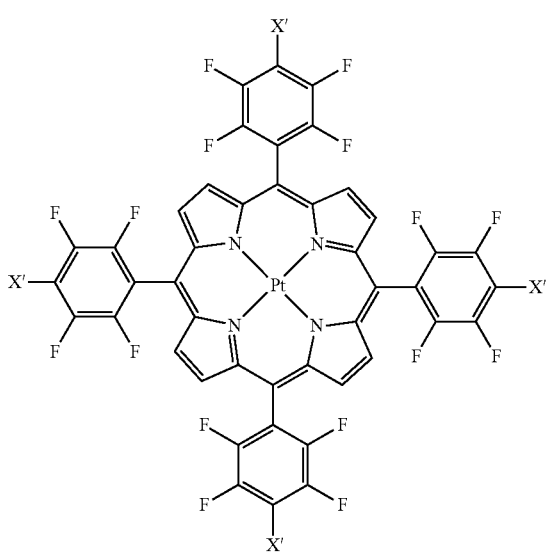

wherein X' is

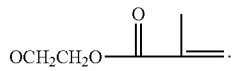

The intra-reference probe has formula III as defined above. In some embodiments, the intra-reference probe is:

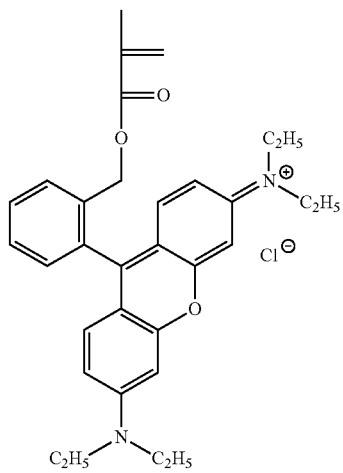 [SMILES: C=C(C)C(=O)OCc1ccccc1-c1c2ccc(=[N+](CC)CC)cc-2oc2cc(N(CC)CC)ccc12 ; [Cl-]]

In the second step of the method, the probe for sensing glucose is attached or immobilized onto the substrate.

The probe for sensing glucose has formula I as defined above. In some embodiments, the probe for sensing glucose is:

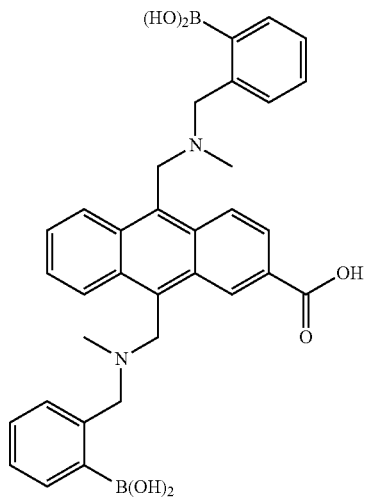 [SMILES: CN(Cc1ccccc1B(O)O)Cc1c2ccccc2c(CN(C)Cc2ccccc2B(O)O)c2cc(C(=O)O)ccc12]

or an activated ester thereof.

In alternate embodiments, the method of preparing an optical fluorescence dual sensor comprises copolymerizing a probe for sensing glucose, a probe for sensing oxygen and an intra-reference probe, with 2-hydroxyethyl methacrylate, N-(6-aminohexyl)methacrylamide, and acrylamide onto a substrate. The probe for sensing glucose, the probe for sensing oxygen and the intra-reference probe are as defined above.

In some embodiments, copolymerizing the probe for sensing glucose, the probe for sensing oxygen and the intra-reference probe, with 2-hydroxyethyl methacrylate, N-(6-aminohexyl)methacrylamide, and acrylamide forms poly(2-hydroxyethyl methacrylate), poly(N-(6-aminohexyl) methacrylamide), poly(acrylamide), poly(2-hydroxyethyl methacrylate)-co-polyacrylamide-co-poly(N-(6-aminohexyl)methacrylamide) and their composites with the polymerized probes.

The present disclosure also provides a method of determining the concentration of glucose in a sample. The method comprises (a) exposing the sample to an optical fluorescence sensor as defined above or an optical fluorescence dual sensor as defined above; (b) irradiating the sensor at a first wavelength to produce a glucose indicator emission signal at a second wavelength and an intra-reference emission signal at a third wavelength; (c) measuring the glucose indicator emission signal at the second wavelength; (d) measuring the intra-reference emission signal at the third emission wavelength; and (e) ratiometrically determining the concentration of glucose in the sample.

The present disclosure also provides a method of determining oxygen concentration in a sample. The method comprises (a) exposing the sample to an optical fluorescence dual sensor as defined above; (b) irradiating the sensor at a first wavelength to produce an oxygen indicator emission signal at a second wavelength and an intra-reference emission signal at a third wavelength; (c) measuring the oxygen indicator emission signal at the second wavelength; (d) measuring the intra-reference emission signal at the third wavelength; and (e) ratiometrically determining the oxygen concentration in the sample.

The present disclosure also provides a method of simultaneously determining the glucose concentration and the oxygen concentration in a sample. The method comprises (a) exposing the sample to an optical fluorescence dual sensor as defined above; (b) irradiating the sensor at a first wavelength to produce a glucose indicator emission signal at a second wavelength, an oxygen indicator emission signal at a third wavelength and an intra-reference emission signal at a fourth wavelength; (c) measuring the glucose indicator emission signal at the second wavelength; (d) measuring the oxygen indicator emission signal at the third wavelength; (e) measuring the intra-reference emission signal at the fourth wavelength; (f) ratiometrically determining the glucose concentration of the sample using the measurements obtained in steps (c) and (e); and (g) ratiometrically determining the oxygen concentration of the sample using the measurements obtained in steps (d) and (e).

In some embodiments, the methods are performed in a high throughput format. In these embodiments, more than one sample is used.

In some embodiments, the sample comprises a bodily fluid. In some aspects of this embodiment, the bodily fluid comprises blood.

In alternate embodiments, the sample is obtained from a cell culture or a subject.

In some embodiments, the sample is selected from the group consisting of live single cells, live several cells, live cell clusters, and live tissue.

BRIEF DESCRIPTION OF THE FIGURES

FIG. 1 also shows the chemical structures of the probes and monomers used in the preparation of an optical dual sensor according to an embodiment of the invention.

FIG. 3A shows absorption spectra with and without glucose. FIG. 3B shows fluorescence intensity by glucose excited at 390 nm. FIG. 3C shows glucose concentration dependent fluorescence intensity ratios at 445 nm. $I_0$ is the intensity at 445 nm without glucose and I is the intensity at 445 nm with various concentrations of glucose.

FIG. 4A shows response of five sensors with tunable weight ratios of HEMA to AM.

FIG. 4B shows responses of another five sensors with tunable MAHA ratios. $I_0$ is the intensity at 445 nm without glucose and 1 is the intensity at 445 nm with glucose.

FIG. 5C shows the time dependent glucose and oxygen concentrations during growth of E. coli detected by a dual sensor according to embodiment of the invention.

DETAILED DESCRIPTION OF THE INVENTION

Figure 1:
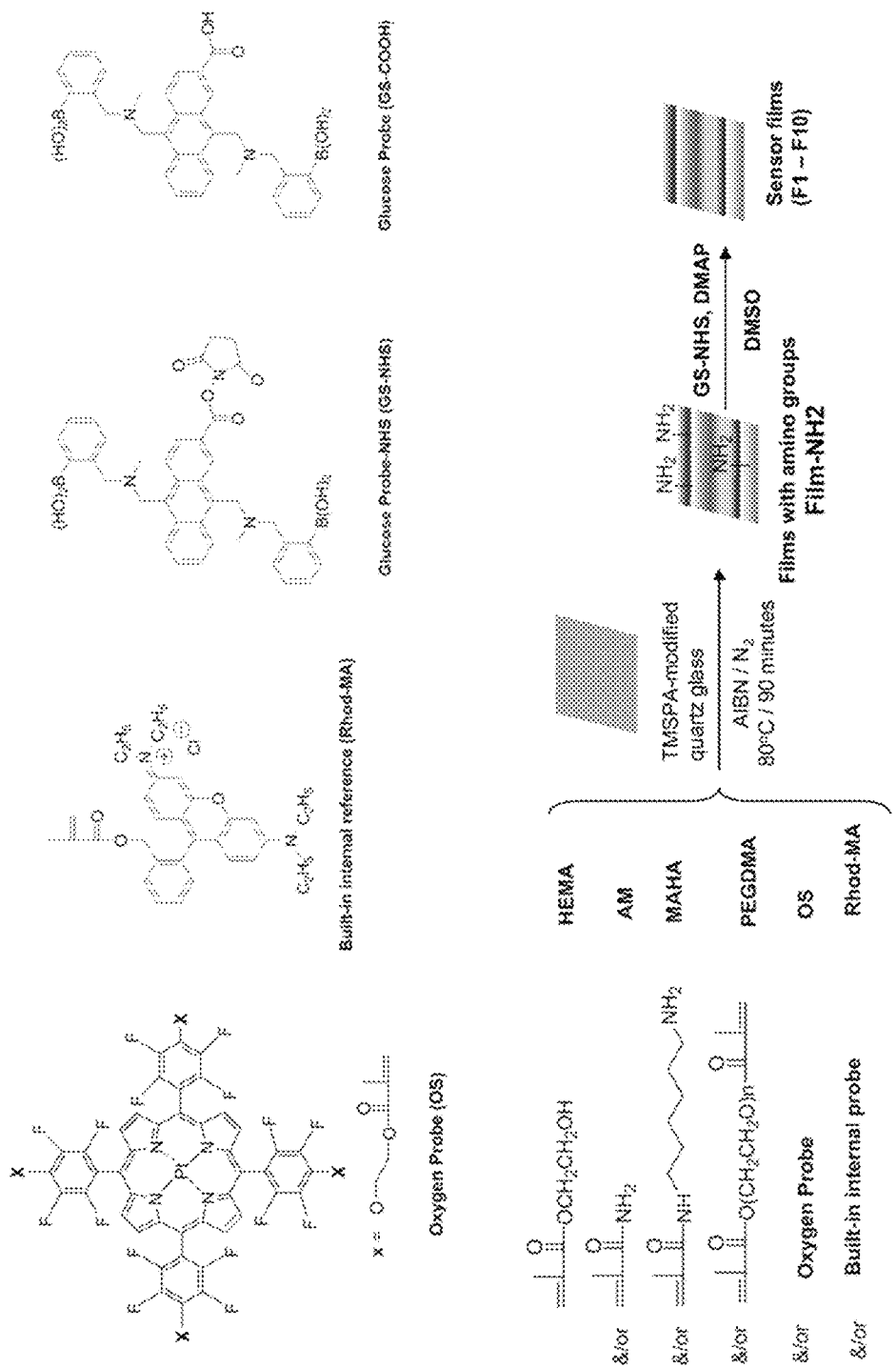
FIG. 1 shows a schematic diagram for preparing an optical fluorescence dual sensor according to an embodiment of the invention.

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "ratiometric method" is based on the measurement of two probes simultaneously, one that is sensitive to the analyte of interest, and a second that is not, and then taking the ratio of the two [31, 32, 33]. The ratiometric method has been known to increase measurement accuracy and to alleviate environmental influences, such as fluctuations in excitation source intensity, variance in probe concentration, and uncontrollable variations in background fluorescence.

The terms "probe for sensing oxygen," "oxygen probe" and "oxygen sensor" are used interchangeably and may be abbreviated as "OS".

The terms "glucose sensor," "glucose probe" and "probe for sensing glucose" are used interchangeably and may be abbreviated as "Glu-Probe" or "GS".

The term "intra-reference probe," "internal reference probe" and "an internal built-in probe" are used interchangeably and may be abbreviated as "IRP".

Sensor Design

The present disclosure provides an optical fluorescence sensor comprising two probes, each with a different emission color. In particular, the sensor comprises a probe for sensing glucose, an intra-reference probe and a matrix.

The probe for sensing glucose has formula I:

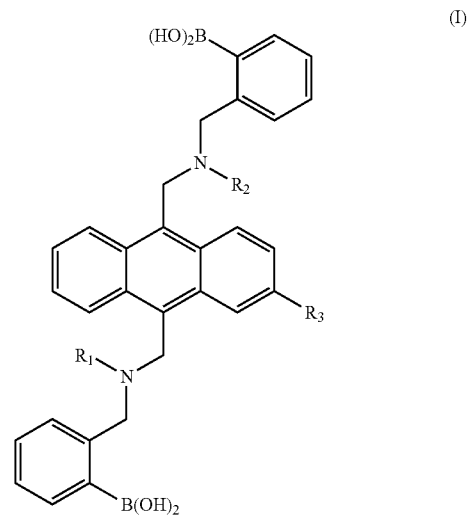

(I)

wherein $R_1$ and $R_2$ can be the same or different and are $C_nH_{2n+1}$, where n is an integer selected from the group consisting of 0, 1, 2, 3, 4, 5, 6, 7 and 8.

$R_3$ is selected from the group consisting of $(CH_2)_mC(O)OH$, $O(CH_2)_mC(O)OH$, $NH(CH_2)_mC(O)OH$, $(CH_2)_mC(O)OR_4$, $O(CH_2)_mC(O)OR_4$, $NH(CH_2)_mC(O)OR_4$, $(CH_2)_mC(O)NH(CH_2)_mNH-A$, $O(CH_2)_mC(O)NH(CH_2)_mNH-A$, $NH(CH_2)_mC(O)NH(CH_2)_mNH-A$, $(CH_2)_mC(O)O(CH_2)_mNH-A$, $O(CH_2)_mC(O)O(CH_2)_mNH-A$, $NH(CH_2)_mC(O)O(CH_2)_mNH-A$, $(CH_2)_mC(O)NH(CH_2)_mNH-M'A$, $O(CH_2)_mC(O)NH(CH_2)_mNH-M'A$, $NH(CH_2)_mC(O)NH(CH_2)_mNH-M'A$, $(CH_2)_mC(O)O(CH_2)_mNH-M'A$, $O(CH_2)_mC(O)O(CH_2)_mNH-M'A$, $NH(CH_2)_mC(O)O(CH_2)_mNH-M'A$, $(CH_2)_mC(O)NH(CH_2)_mNH-VA$, $O(CH_2)_mC(O)NH(CH_2)_mNH-VA$, $NH(CH_2)_mC(O)NH(CH_2)_mNH-VA$, $(CH_2)_mC(O)O(CH_2)_mNH-VA$, $O(CH_2)_mC(O)O(CH_2)_mNH-VA$, $NH(CH_2)_mC(O)O(CH_2)_mNH-VA$.

m is an integer selected from the group of consisting of 0, 1, 2, 3, 4, 5, 6, 7, 8, 9, 10, 11 and 12.

$R_4$ is an activating group. Activating groups are well-known in the art and any can be used as $R_4$.

M'A is

A is

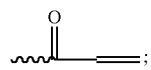

and VA is

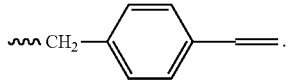

In some embodiments, $R_1$ is $C_nH_{2n+1}$, where n is an integer selected from the group consisting of 0, 1, 2, 3, 4, 5 and 6. In other embodiments, $R_1$ is $C_nH_{2n+1}$, where n is an integer selected from the group consisting of 0, 1, 2 and 3. In some embodiments, $R_1$ is $CH_3$.

In some embodiments, $R_2$ is $C_nH_{2n+1}$, where n is an integer selected from the group consisting of 0, 1, 2, 3, 4, 5 and 6. In other embodiments, $R_2$ is $C_nH_{2n+1}$, where n is an integer selected from the group consisting of 0, 1, 2 and 3. In some embodiments, $R_2$ is $CH_3$.

In some embodiments, $R_3$ is selected from the group consisting of $(CH_2)_mC(O)OH$, $O(CH_2)_mC(O)OH$, $NH(CH_2)_mC(O)OH$, $(CH_2)_mC(O)OR_4$, $O(CH_2)_mC(O)OR_4$ and $NH(CH_2)_mC(O)OR_4$. In other embodiments, $R_3$ is selected from the group consisting of $(CH_2)_mC(O)OH$, $O(CH_2)_mC(O)OH$, $(CH_2)_mC(O)OR_4$ and $O(CH_2)_mC(O)OR_4$. In some embodiments, $R_3$ is $(CH_2)_mC(O)OH$ or $(CH_2)_mC(O)OR_4$.

In some embodiments, m is an integer selected from the group of consisting of 0, 1, 2, 3, 4, 5 and 6. In other embodiments, m is an integer selected from the group of consisting of 0, 1, 2 and 3. In some embodiments, m is an integer selected from the group of consisting of 0.

In some embodiments, $R_4$ is an activating group selected from the group consisting of N-hydroxysuccinimide, p-nitrophenyl, pentafluorophenyl, 2,4,5-trichlorophenyl, pentachlorophenyl and 4-oxo-3,4-dihydrobenzotriazin-3-yl. In some embodiments, $R_4$ is N-hydroxysuccinimide.

In some embodiments, the probe for sensing glucose is:

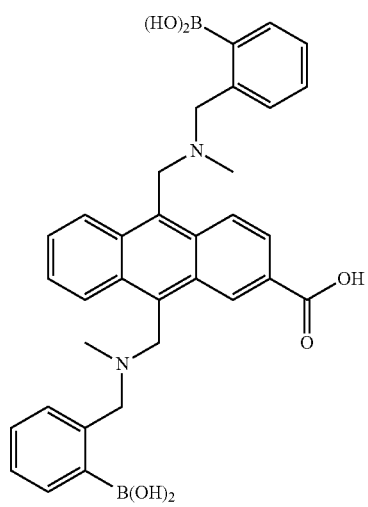 [SMILES: CN(Cc1ccccc1B(O)O)Cc1c2ccccc2c(CN(C)Cc2ccccc2B(O)O)c2cc(C(=O)O)ccc12]

or an activated ester thereof.

The intra-reference probe has formula III:

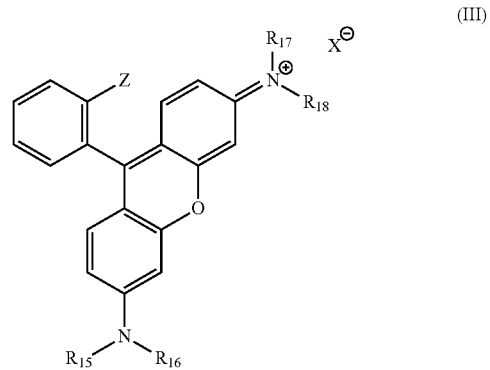

wherein $R_{15}$, $R_{16}$, $R_{17}$, and $R_{18}$ is can be the same or different and are $C_2H_{2n+1}$, where n is an integer selected from the group consisting of 1, 2, 3, 4, 5, 6, 7 and 8;

X is an anion. Any anion known in the art can be used as X.

Z is selected from the group consisting of: $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, $CH_2(OCH_2CH_2)_rOVA$, wherein M'A, A and VA are as defined above.

p is an integer selected from the group of consisting of 1, 2, 3, 4, 5, 6, 7, 8, 9, 10, 11 and 12.

q is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

r is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

In some embodiments, $R_{15}$ is $C_nH_{2n+1}$, where n is an integer selected from the group consisting of 0, 1, 2, 3, 4, 5 and 6. In other embodiments, $R_{15}$ is $C_nH_{2n+1}$, where n is an integer selected from the group consisting of 0, 1, 2 and 3. In some embodiments, $R_{15}$ is $C_2H_5$.

In some embodiments, $R_{16}$ is $C_nH_{2n+1}$, where n is an integer selected from the group consisting of 0, 1, 2, 3, 4, 5 and 6. In other embodiments, $R_{17}$ is $C_nH_{2n+1}$, where n is an integer selected from the group consisting of 0, 1, 2 and 3. In some embodiments, $R_{18}$ is $C_2H_5$.

In some embodiments, $R_{17}$ is $CH_nH_{2n+1}$, where n is an integer selected from the group consisting of 0, 1, 2, 3, 4, 5 and 6. In other embodiments, $R_{17}$ is $C_nH_{2n+1}$, where n is an integer selected from the group consisting of 0, 1, 2 and 3. In some embodiments, $R_{17}$ is $C_2H_5$.

In some embodiments, $R_{18}$ is $C_nH_{2n+1}$, where n is an integer selected from the group consisting of 0, 1, 2, 3, 4, 5 and 6. In other embodiments, $R_{18}$ is $C_nH_{2n+1}$, where n is an integer selected from the group consisting of 0, 1, 2 and 3. In some embodiments, $R_{18}$ is $C_2H_5$.

In some embodiments, X is selected from the group consisting of fluoride, chloride, bromide, iodide, hydroxide, methyl sulfate, hydrogen carbonate, dihydrogen phosphate. In other embodiments, X is selected from the group consisting of fluoride, chloride, bromide and iodide. In some embodiments, X is chloride.

In some embodiments, Z is selected from the group consisting of: $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, and $CH_2(OCH_2CH_2)_rOVA$. In other embodiments, Z is selected from the group consisting of: $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$ and $NH(CH_2)_pOVA$. In some embodiments, Z is selected from the group consisting of: $(CH_2)_pOM'A$, $O(CH_2)_pOM'A$, $NH(CH_2)_pOM'A$ and $(CH_2)_pOA$. In some embodiments, Z is $(CH_2)_pOM'A$.

In some embodiments, p is an integer selected from the group of consisting of 1, 2, 3, 4, 5 and 6. In other embodiments, p is an integer selected from the group of consisting of 1, 2 and 3. In some embodiments, p is 1.

In some embodiments, q is an integer selected from the group of consisting of 1, 2, 3, 4, 5 and 6. In other embodiments, q is an integer selected from the group of consisting of 1, 2 and 3. In some embodiments, q is 1.

In some embodiments, r is an integer selected from the group of consisting of 1, 2, 3, 4, 5 and 6. In other embodiments, r is an integer selected from the group of consisting of 1, 2 and 3. In some embodiments, r is 1.

In some embodiments, the intra-reference probe is:

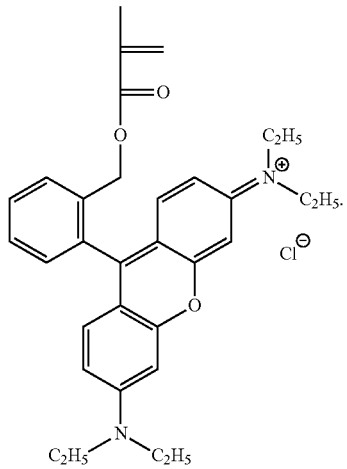 [SMILES: C=C(C)C(=O)OCc1ccccc1-c1c2ccc(=[N+](CC)CC)cc-2oc2cc(N(CC)CC)ccc12 ; [Cl-]]

Figure 2:
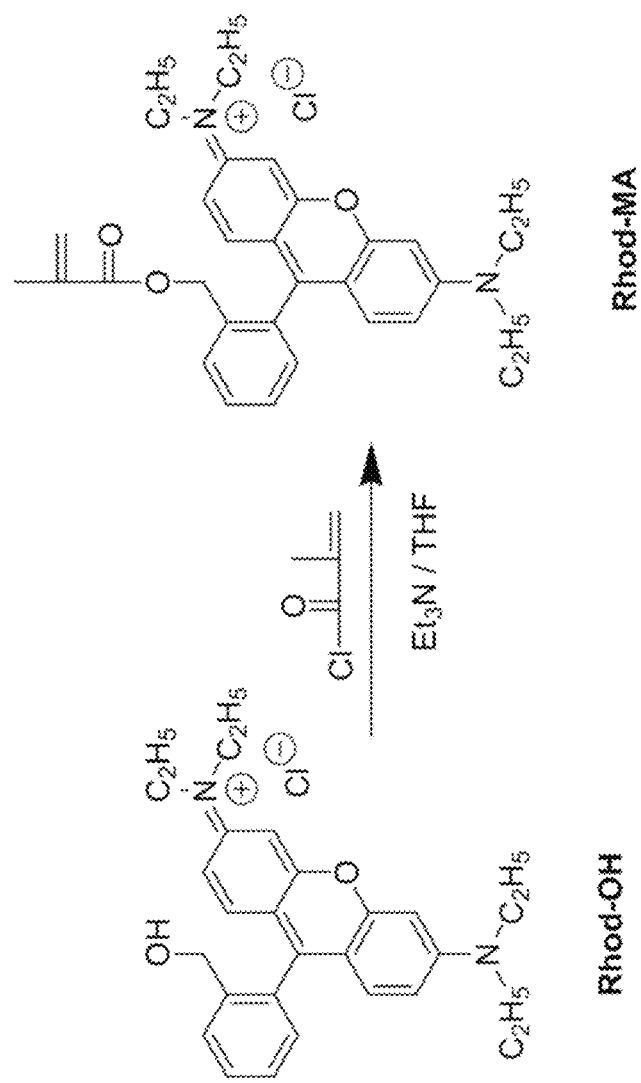
FIG. 2 shows the synthesis of Rhod-MA, an interference probe according to an embodiment of the invention.

The intra-reference probe does not respond to either glucose or $O_2$. The intra-reference probe can be synthesized, as shown in FIG. 2.

The matrix comprises a polymer selected from the group consisting of acrylamide, N-(6-aminohexyl)methacrylamide, and poly(ethylene glycol) dimethacrylate, methoxy-poly(ethylene glycol) methacrylate, 2-hydroxyethyl methacrylate and combinations thereof. In some embodiments, the matrix is a polyacrylamide-based matrix.

The present disclosure also provides an optical fluorescence dual sensor comprising three probes, each with a different emission color. In particular, the sensor comprises a probe for sensing glucose, a probe for sensing oxygen, an intra-reference probe and a matrix. The probe for sensing glucose, the intra-reference probe and matrix are as defined above.

The probe for sensing oxygen has formula II:

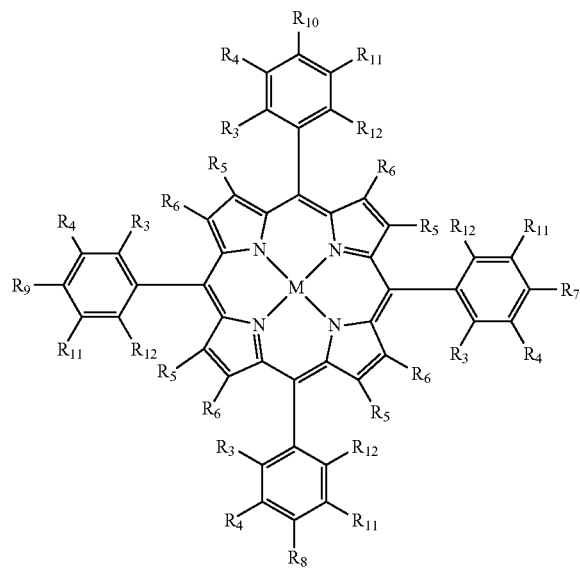

where

M is selected from Pt or Pd.

$R_{11}$ and $R_{12}$ can be the same or different and are independently selected from the group consisting of H, F, Cl, Br, I, $CH_3$, $OCH_3$ and $OC_2H_5$.

$R_3$ and $R_4$ can be the same or different and are independently selected from the group consisting of H, F, Cl, Br, I, $CH_3$, $OCH_3$ and $OC_2H_5$.

$R_5$ and $R_6$ can be the same or different and are independently selected from the group consisting of H, F, Cl, Br, I, $CH_3$, $OCH_3$ and $OC_2H_5$.

$R_7$, $R_8$, $R_9$ and $R_{10}$ can be the same or different and are independently selected from the group consisting of $(CH_2)_pOH$, $O(CH_2)_pOH$. $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, where M'A is

A is

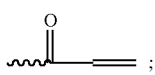

VA is

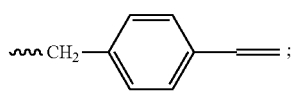

p is an integer selected from the group of consisting of 2, 3, 4, 5, 6, 7, 8, 9, 10, 11 and 12.

q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

In some embodiments, M is Pt.
In some embodiments, $R_{11}$ is F.
In some embodiments, $R_{12}$ is F.
In some embodiments, $R_3$ is F.
In some embodiments, $R_4$ is F.
In some embodiments, $R_5$ is H.
In some embodiments, $R_6$ is H.
In some embodiments, $R_7$ is $O(CH_2)_pOM'A$. In some aspects of this embodiment, p is 2.
In some embodiments, $R_8$ is $O(CH_2)_pOM'A$. In some aspects of this embodiment, p is 2.
In some embodiments, $R_9$ is $O(CH_2)_pOM'A$. In some aspects of this embodiment, p is 2.
In some embodiments, $R_{10}$ is $O(CH_2)_pOM'A$. In some aspects of this embodiment, p is 2.
In some embodiments, the probe for sensing oxygen is:

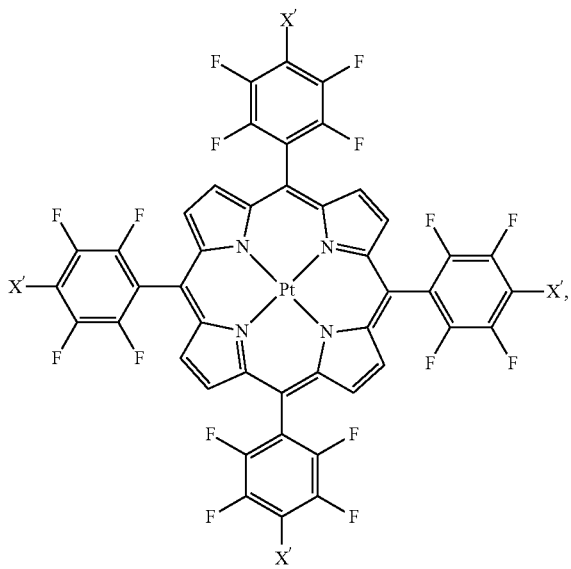

wherein X' is

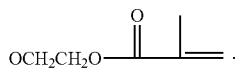

In some embodiments, the oxygen probe is a platinum porphyrin derivative exhibiting red emission, which can be quenched by $O_2$ through triplet-triplet energy transfer.

The glucose probe, the $O_2$ probe, and the intra-reference probe each have a different emission color. In some embodiments, the three optical probes have well separated spectral windows. In some embodiments, the three optical probes can be excited using the same excitation wavelength. In preferred embodiments, the three optical probes can be excited at a wavelength of about 445 nm.

Methods of Preparing the Sensors

The present disclosure also provides a method of preparing an optical fluorescence sensor. In the first step, an intra-reference probe is copolymerized with 2-hydroxyethyl methacrylate, N-(6-aminohexyl)methacrylamide, and acrylamide onto a substrate.

The substrate is preferably trimethylsilylpropyl acrylate modified PET, glass or quartz glass.

In some embodiments, the copolymerization is performed at a temperature ranging from about 60 to about 100° C., preferably about 80° C. In some embodiments, the copolymerization is performed under vacuum or nitrogen.

In some embodiments, copolymerizing the intra-reference probe, with 2-hydroxyethyl methacrylate, N-(6-aminohexyl) methacrylamide, and acrylamide forms poly(2-hydroxyethyl methacrylate), poly(N-(6-aminohexyl) methacrylamide), poly(acrylamide), poly(2-hydroxyethyl methacrylate)-co-polyacrylamide-co-poly(N-(6-aminohexyl)methacrylamide) and their composites with the polymerized probe.

In the second step, a probe for sensing glucose is attached or immobilized onto the substrate. The probe for sensing glucose is as defined above. The probe for sensing glucose can be attached or immobilized onto the substrate using methods known in the art. In some embodiments, the probe for sensing glucose is attached or immobilized onto the substrate via coupling with amino-groups on the copolymer formed in step one. In other embodiments, the probe for sensing glucose is attached or immobilized onto the substrate via coupling with azido groups on the copolymer formed in step one. Such coupling can be performed using. e.g., Click chemistry. In these embodiments, the glucose probe comprises an acetylene group.

In alternate embodiments, the method of preparing an optical fluorescence sensor comprises the step of copolymerizing a probe for sensing glucose and an intra-reference probe, with 2-hydroxyethyl methacrylate, N-(6-aminohexyl) methacrylamide, and acrylamide onto a substrate. The probe for sensing glucose has formula (I) as defined above and the intra-reference probe has formula (III) as defined above.

In some embodiments, copolymerizing the probe for sensing glucose and the intra-reference probe, with 2-hydroxyethyl methacrylate, N-(6-aminohexyl)methacrylamide, and acrylamide forms poly(2-hydroxyethyl methacrylate), poly(N-(6-aminohexyl)methacrylamide), poly (acrylamide), poly(2-hydroxyethyl methacrylate)-co-polyacrylamide-co-poly(N-(6-aminohexyl)methacrylamide) and their composites with the polymerized probes.

The present invention also provides a method of preparing an optical fluorescence dual sensor. In the first step of the method, a probe for sensing oxygen, and an intra-reference probe are copolymerized with poly(2-hydroxyethyl methacrylate), polyacrylamide, and poly(2-hydroxyethyl methacrylate)-co-polyacrylamide onto a substrate.

The probe for sensing oxygen has formula II as defined above.

The intra-reference probe has formula III as defined above.

In the second step of the method, the probe for sensing glucose is attached or immobilized onto the substrate.

The probe for sensing glucose has formula I as defined above.

In alternate embodiments, the method of preparing an optical fluorescence dual sensor comprises copolymerizing a probe for sensing glucose, a probe for sensing oxygen and an intra-reference probe, with 2-hydroxyethyl methacrylate, N-(6-aminohexyl)methacrylamide, and acrylamide onto a substrate. The probe for sensing glucose, the probe for sensing oxygen and the intra-reference probe are as defined above.

In some embodiments, copolymerizing the probe for sensing glucose, the probe for sensing oxygen and the intra-reference probe, with 2-hydroxyethyl methacrylate, N-(6-aminohexyl)methacrylamide, and acrylamide forms poly(2-hydroxyethyl methacrylate), poly(N-(6-aminohexyl) methacrylamide), poly(acrylamide), poly(2-hydroxyethyl methacrylate)-co-polyacrylamide-co-poly(N-(6-aminohexyl)methacrylamide) and their composites with the polymerized probes.

Methods of Using the Sensors

The present disclosure provides a method of determining the concentration of glucose in a sample. The method comprises exposing a sample to an optical fluorescence sensor or optical fluorescence dual sensor. The sensors can be any of the sensors described above.

The sensor is then irradiated at a first wavelength to produce a glucose indicator emission signal at a second wavelength and an intra-reference emission signal at a third wavelength. The glucose indicator emission signal is measured at the second wavelength and the intra-reference emission signal is measured at the third emission wavelength. The concentration of glucose in the sample is then determined ratiometrically.

In some embodiments, the first wavelength is about 390 nm.

In some embodiments, the second wavelength is about 445 nm.

In some embodiments, the third wavelength is about 580 nm.

In some embodiments, this method of determining the concentration of glucose in a sample can be used in methods to detect, monitor or treat diabetes.

The present invention also provides a method of determining the concentration of oxygen in a sample. The method comprises exposing the sample to an optical fluorescence dual sensor. The optical fluorescence dual sensor can be any of the sensors described above.

The sensor is then irradiated at a first wavelength to produce an oxygen indicator emission signal at a second wavelength and an intra-reference emission signal at a third wavelength. The oxygen indicator emission signal is measured at the second wavelength and the intra-reference emission signal is measured at the third wavelength. The oxygen concentration in the sample is then determined ratiometrically.

In some embodiments, the first wavelength is about 390 nm.

In some embodiments, the second wavelength is about 580 nm.

In some embodiments, the third wavelength is about 650 nm.

The present invention additionally provides a method of simultaneously determining the glucose concentration and the oxygen concentration in a sample. The method comprises exposing the sample to an optical fluorescence dual sensor. The optical fluorescence dual sensor can be any of the sensors described above.

The sensor is irradiated at a first wavelength to produce a glucose indicator emission signal at a second wavelength, an oxygen indicator emission signal at a third wavelength and an intra-reference emission signal at a fourth wavelength. The glucose indicator emission signal is measured at the second wavelength, the oxygen indicator emission signal is measured at the third wavelength and the intra-reference emission signal is measured at the fourth wavelength. The glucose concentration of the sample is then determined ratiometrically using the measurements obtained at the second and fourth wavelengths; and the oxygen concentration of the sample is determined ratiometrically using the measurements obtained at the third and fourth wavelengths.

In some embodiments, the first wavelength is about 390 nm.

In some embodiments, the second wavelength is about 445 nm

In some embodiments, the third wavelength is about 580 nm.

In some embodiments, the fourth wavelength is about 650 nm.

In each of the methods described above, more than one sample can be used. Thus, the method can be performed in a high throughput format.

In each of the methods described above, the samples can be monitored in real-time for changes in their glucose and/or oxygen concentration.

In some of the methods described above, the sample comprises a bodily fluid. As used herein, the term "bodily fluid" refers to any desired fluid to be sampled, and includes, but is not limited to, blood, cerebrospinal fluid, interstitial fluid, dermal fluid, semen, sweat, saliva, tears, urine and the like.

The term "blood" in the context of the invention includes whole blood and its cell-free components, namely, plasma and serum.

In some of the methods described above, the sample can be obtained from a subject. As used herein, the term "subject" refers to an animal, preferably, a mammal, and most preferably, a human. In some aspects of this embodiment, the sample comprises mammalian cells.

In some embodiments, the sample is selected from the group consisting of live single cells, live several cells, live cell clusters, and live tissue. In some aspects of this embodiment, the sample comprises bacterial cells, such as *Escherichia coli* (*E. coli*) or *Bacillus subtilis* (*B. subtilis*).

Devices Comprising the Sensors and Methods of Using the Same

The present disclosure provides a chamber device for analyzing living cell(s). Such a device comprises a base and a lid that when reversibly pressed closed create a chamber; the base being configured with an optically transparent well to contain at least one living cell; the lid having a thin, sensor coating comprising at least one sensor which goes through the chamber seal: wherein when pressed together the lid and the base create a seal. The sensor can be any of the sensors described above.

In some embodiments, the sensor coating is made at a thickness of preferably about 1 um. Such a coating may be achieved by fabricating about 1 um shim using photoresist patterned by photolithography and having the shim is aligned along two or more edges of the substrate allowing the sensor to be filled in the interior area while controlling thickness of the sensor.

In some embodiments, the chamber device comprises multiple sensors. In some aspects, the chamber device comprises two sensors. In other aspects, the chamber device comprises three sensors.

In some embodiments, the sensor is patterned in such a manner that multiple sensors can be exposed to the well interior and exterior, and traversing the seal. The sensors may be mechanical aligned.

In some embodiments, the chamber device comprises a foreign material. In this embodiment, the sensor is of sufficient thickness and compliance as to accommodate the foreign material and variation in both substrate and sensor surface finish while enabling an adequate seal. This compliance may be in addition to compliance provided by the well substrate, or in place of it.

The present disclosure also provides methods of using the chamber device.

In one embodiment, the method comprises determining the respiration rate of a cell using a chamber device. The chamber device can be any of the chamber devices described above. The step of determining the respiration rate of a cell comprises measuring the oxygen concentration inside the well for the cell.

In a second embodiment, the method comprises performing phenotypic measurements of cells using a chamber device. The chamber device can be any of the chamber devices described above. The step of performing phenotypic measurements comprises measuring the oxygen concentration inside the well for a plurality of cells.

In a third embodiment, the method comprises detecting a leak in the chamber device. The chamber device can be any of the chamber devices described above. The step of detecting a leak comprises measuring the oxygen concentration inside and outside the chamber device.

In some aspects of the third embodiment, a gas comprising a known amount of oxygen is applied to the perimeter of the chamber after sufficient cellular respiration data is collected in order to correct for oxygen leakage through the seal.

In a fourth embodiment, the method comprises seeding cells in the well and excluding cells from outside of the wells. In some aspects of this embodiment, the cells are excluded from outside of the wells by transverse liquid flow.

In order that this invention be more fully understood, the following examples are set forth. These examples are for the purpose of illustration only and are not to be construed as limiting the scope of the invention in any way.

Examples

Materials and Reagents

All chemicals and solvents were of analytical grade and were used without further purification. Glucose, 2-acetyl-9,10-dimethylanthracene, N-bromosuccinimide, triethylamine, dichloromethane, tetrahydrofuran (THF), methanol, methylamine, methacryloyl chloride, hexamethylenediamine, N,N'-dimethylformamide (DMF), dimethyl sulfoxide (DMSO), 2-hydroxyethyl methacrylate (HEMA), acrylamide (AM), N-hydroxysuccinimide (NHS), 4-dimethylaminopyridine (DMAP), N,N'-dicyclohexylcarbodiimide (DCC), 3-(trimethoxysilyl)propyl acrylate (TMSPA), poly(ethylene glycol) dimethacrylate (PEGDMA, Mn=550), and azobisisobutyronitrile (AIBN) were commercially available from Sigma-Aldrich and used without further purification. Oxygen probe (OS, FIG. 1), and glucose probe (GS) were prepared according to known procedures [26, 30]. Precursor for built-in internal reference probe (Rhod-OH, FIG. 2) was prepared according to a published procedure [36]. 6-Aminohexyl methacrylamide (MAHA) was synthesized according to a modified procedure in literature [37]. Doubly distilled water was used for the preparation of buffer solutions. The pH values were determined with a digital pH meter (Thermo Electron Corporation, Beverly, Mass.) calibrated at room temperature with standard buffers. For fluorescence measurements, quartz glass from University Wafer (South Boston, Mass.) were cut into square of 13 mm×13 mm using a dicing saw (Microautomation, Billerica, Mass.).

Instruments

A Varian liquid-state NMR operated at 400 MHz for $^1$H NMR was used for NMR spectra measurements. MALDI-TOFF mass were performed by the ASU Mass Spectrometry Laboratory. An oxygen plasma cleaner (Harrick Plasma. Ithaca, N.Y.) was used for quartz glass surface activation. A Shimadzu UV-3600 UV-Vis-NIR spectrophotometer (Shimadzu Scientific Instruments, Columbia, Md.) was used for absorbance measurements. A Shimadzu RF-5301 spectrofluorophotometer was used for fluorescence measurements. For easy measurement of the films in liquid solutions, quartz glass was cut with a dicing saw into squares of 13 mm×13 mm, which can fit diagonally into a quartz fluorescence cuvette to enable the sensing membrane be positioned at an angle of 45° to the excitation light.

Synthesis of NHS Activated Glucose Probe (GS-NHS)

A mixture containing 500 mg of GS-COOH (0.87 mmol) [26], 303 mg of DCC (1.47 mmol), 201 mg of NHS (1.75 mmol), 213 mg of DMAP (1.75 mmol), and 20 mL of DMSO was stirred at room temperature for 16 hours. Precipitation was removed by filtration. The reaction mixture was diluted with 150 mL of dichloromethane, washed with water three times and with saturated aqueous sodium chloride and dried. The solution was evaporated. (600 mg of the GS-NHS with a yield of 100% was obtained and was used for the next reaction (immobilization) without further purification.

Synthesis of the Built-in Internal Reference Probe (Rhod-Ma)

Rhod-MA was synthesized according to FIG. 2. 400 mg (0.86 mmol) of Rhod-OH and triethyl amine (261 mg, 2.58 mmol) were dissolved in 20 mL of THF. 135 mg of methacryloyl chloride (135 mg, 1.30 mmol) in 2 mL THF was added into the above mixture slowly at 0-5° C. The reaction was stirred at room temperature overnight. The mixture poured into water. Organic materials were extracted into methylene chloride and the organic phase was washed with water three times. After drying over $MgSO_4$, the product of Rhod-MA was purified by column Chromatography with methylene chloride/methanol (95:5 by volume). Yield: 300 mg (66%). Yield: 65%. $^1$H NMR (δ, ppm, $CDCl_3$): 7.63 (m, 3H), 7.38 (d, 1H), 6.96 (m, 6H), 5.64 (s, 1H), 5.38 (s, 1H), 4.92 (s, 2H), 3.60 (m, 8H), 1.16 (t, 12H). MOLFI-TOF (m/z): 497.77 (calc: $C_{32}H_{37}N_2O_3^+$, M-Cl$^-$, 497.28).

Preparation of Sensor Films

Glucose Only Sensor Thin Films

Sensor film was prepared through two steps. The first step is to prepare a film with amino-groups on the surface (Film-NH$_2$). The second step is to graft the GS-NHS onto the amino-containing film to form glucose sensor film (F1-F5). Preparation of the film of Film-NH$_2$ was followed our published protocol [30, 38]. A typical example is provided below. Briefly, AM (165 mg), PEGDMA (35 mg), MAHA (16.5 mg), and AIBN (6 mg) were dissolved in 1 mL DMF as a stock solution. 15 µL of the stock solution was added onto the surface of TMSPA treated quartz glass and covered with a clean but untreated cover slip to make a sandwich structure. The modification of TMSPA on the surface of quartz glass was to enable the sensor and matrices to be chemically grafted onto a quartz substrate [30]. To produce the polymer thin film with good mechanical stability, PEGDMA was used as a cross-linker. MAHA was applied to introduce active reaction group for the immobilization of glucose sensor onto the thin film later on. The thickness was controlled by the use of 25-µm Kapton tape (DuPont, Wilmington, Del.). The sandwich set-up was placed into a vacuum oven, which was then evacuated and refilled with nitrogen three times. Polymerization was carried out under nitrogen at 80° C. for 90 minutes in the oven. The quartz glasses with polymer membranes were removed from the oven, with Kapton tape and no-surface modified cover slip being removed from the polymerized membrane surface. For matrices optimization, different ratios of AM/HEMA/MAHA (Table 1) were used in the polymerization process to form various films with different amounts of amino groups for tuning the density of the glucose probes in the sensor films. The obtained amino group-containing films were put in a flat bottom bottle containing 1.0 mL of DMSO, 3.0 mg of DMAP and 0.45 mg of GS-NHS to graft glucose probe onto the films. 16 hours later, the films were taken out and washed with methanol to remove any remaining non-reacted compounds and residual solvent. The films were dried and stored in the dark at room temperature.

TABLE 1

Compositions of thin films of F1 to F9 and their sensitivity

| Films | PHEMA | PAM | Percentage of probe linker (MAHA) in total weight of polymer compositions | Sensitivity ($I_{100\ mM}/I_{0\ mM}$) |
|---|---|---|---|---|
| F1 | 100 | 0 | 7.5 | 3.2 |
| F2 | 85 | 15 | 7.5 | 4.0 |
| F3 | 50 | 50 | 7.5 | 7.6 |
| F4 | 10 | 90 | 7.5 | 8.3 |
| F5 | 0 | 100 | 7.5 | 9.8 |
| F6 | 0 | 100 | 3.3 | 10.3 |
| F7 | 0 | 100 | 11 | 9.2 |
| F8 | 0 | 100 | 15 | 9.7 |
| F9 | 0 | 100 | 22 | 9.1 |

Triple Color Glucose-Oxygen Dual Sensor

Films were prepared following the above described procedure for F5 (Table 1), while adding OS and Rhod-MA in the mixture of monomers for film preparation. Ratios of OS and Rhod-MA were fixed at 0.32% and 0.1% of total material weight, respectively. Triple color glucose-oxygen dual sensing film (F10) was formed by grafting glucose probe onto the film with amino moieties.

Sensor Characterization

Sensor performance was characterized using a spectrofluorophotometer. A sensor film with a 1.3×1.3 cm dimension was placed diagonally in a cuvette with 2 mL of liquid (either a buffer or a medium) with a 45° facing angel to the excitation light. All of the probes used herein could be excited efficiently at 390 nm and their emissions were collected from 410 to 700 nm. During the titration at each condition, the film was equilibrated for 30 second and then the data were collected. Glucose concentrations were varied from 0 to 100 mM in solutions and the concentrations of the dissolved oxygen were tuned from 0 to 41 mg/L, or 0 to 41 ppm, corresponding to oxygen partial pressures of 0 to 100% of atmospheric pressure by bubbling gas oxygen into the liquid for 2 minutes. Note at 23° C., the dissolved oxygen concentration in water is 8.6 mg/L.

Culture of E. Coli and B. subtilis for Extracellular Sensing

E. coli (JM109) or B. subtilis (168) were cultured in Luria-Bertani broth overnight at 37° C. with vigorous shaking. The concentrations of bacteria in culture were estimated by measuring the optical density at 600 nm (OD600). OD600 value of 1 indicates 5.0×108 cfu·mL$^{-1}$ (colony-forming units per milliliter) for E. coli and indicates 2.25× 108 cfu·mL$^{-1}$ for B. subtilis [38, 39]. Bacteria in 1 mL of culture was collected by spin-down and resuspended in 10 mL of testing medium containing 7.0 g K$_2$HPO$_4$, 3.0 g KH$_2$PO$_4$, 1.0 g (NH$_4$)$_2$SO$_4$, 0.5 g sodium citrate, 0.1 g MgSO$_4$·7H$_2$O, 5.0 mg CaCl$_2$, 0.25 mg FeSO$_4$, 0.2% Casamino acids (BD Diagnostic Systems, Sparks, Md.) in 1.0 liter of medium [14, 42]. After vigorous shaking at 37° C. for 2 hours, the cell concentration of culture was determined. According to the amount of cells needed for the experiment, bacteria was harvested from an appropriate volume of culture by a spin-down process followed by washing once with testing medium that does not contain glucose. The final pellet was re-suspended into testing medium with 10 mM of glucose to achieve the required concentration for experiments.

Culture of HeLa Cells and J774 for Extracellular Sensing

Both HeLa and J774 cell lines were purchased from American Type Culture Collection (ATCC, Manassas, Va.). Cells were cultured in Dulbecco's Modified Eagle Medium (DMEM) supplemented with 10% fetal bovine serum (FBS), 1% penicillin/streptomycin and incubated at 37° C. in a 5% CO$_2$ atmosphere. Cells were harvested and washed with KRH buffer (50 mM of HEPES, 137 mM of NaCl, 4.7 mM of KCl, 1.85 mM of CaCl$_2$, 1.3 mM of MgSO$_4$ and 0.1% BSA) for three times [2,14]. Fluorescence assays were performed immediately after cells were re-suspended into KHR buffer containing 10 mM of glucose.

The Use of the Triple Color Dual Glucose and Oxygen for Simultaneously Monitoring Glucose and Oxygen Consumptions The sensor film F10 was placed into a 4 mL cuvette with 2 mL of with cell culture media with different species and densities. In order to prevent the exchange of oxygen in the media with air, 0.5 mL of mineral oil was added on the top of the media. Time dependent fluorescence change was monitored. According to the calibration curve of the use of the same sensor, glucose and/or oxygen concentrations were calculated.

Results and Discussion

Design of Sensor

Figure 10:
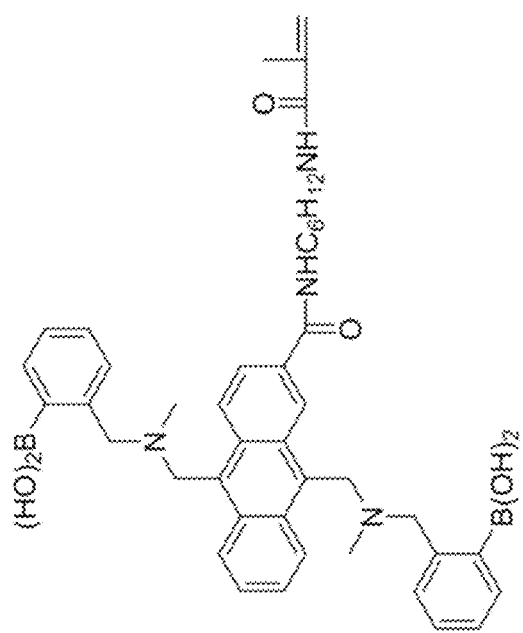
FIG. 10 shows the structure of the monomeric glucose probe GS-MA.

The sensors of the present disclosure are in the thin film state and the probes were chemically immobilized in the matrices where there is no leaching problem of the probes from the matrices. Further, the matrices were chemically grafted on the substrate quartz glass; thus, the sensor is robust, reversible, and stable. Initially, we synthesized a polymerizable glucose probe (GS-MA, FIG. 10) and polymerized this probe in PHEMA-co-PAM matrixes. This process of creating a glucose sensor resulted in a sensor of low sensitivity. (data not shown). After GS-NHS (FIG. 1) was chemically grafted onto the amino-containing polymer film, we found the sensitivity of the glucose sensor improved significantly. Therefore, the sensor synthesis followed the procedure as illustrated in FIG. 1. In order to achieve a high selectivity to glucose, the glucose probe with two boronic acid moieties was chosen because of its known high selectivity to glucose [25]. For oxygen sensing, we chose the modified perfluoro-platinum porphyrin, OS, with four cross-linkable/polymerizable methacrylate moieties, which was demonstrated to be an excellent oxygen probe in various matrices [30, 43]. To enable simultaneous analyses of both the glucose and oxygen concentrations, a dual glucose and oxygen sensor was synthesized. To achieve an accurate analyses of the glucose and oxygen concentrations in biological conditions, the dual glucose and oxygen sensor possesses an internal "built-in" probe (Rhod-MA, FIG. 1), which does not respond to either glucose or oxygen. Therefore, the ratiometric approach can be used for accurate analyses of glucose and oxygen concentrations. The ratiometric approach has been demonstrated as an efficient approach for biological analysis with little interference by the sensor's local concentrations, non-uniformity, biological backgrounds, and environment [31-35]. We chose the biocompatible poly(2-hydroxyethyl methacrylate) (PHEMA), polyacrylamide (PAM), and their composites as the matrices [44, 45]. A dimethacrylate moieties-containing poly(ethylene glycol) (PEGDAM) was used as a crosslinker to further make the film robust.

Optimization of the Glucose Sensor Films

Influences of Matrices (the Ratio of PHMA to PAM) on Sensor Performances

Figure 3:
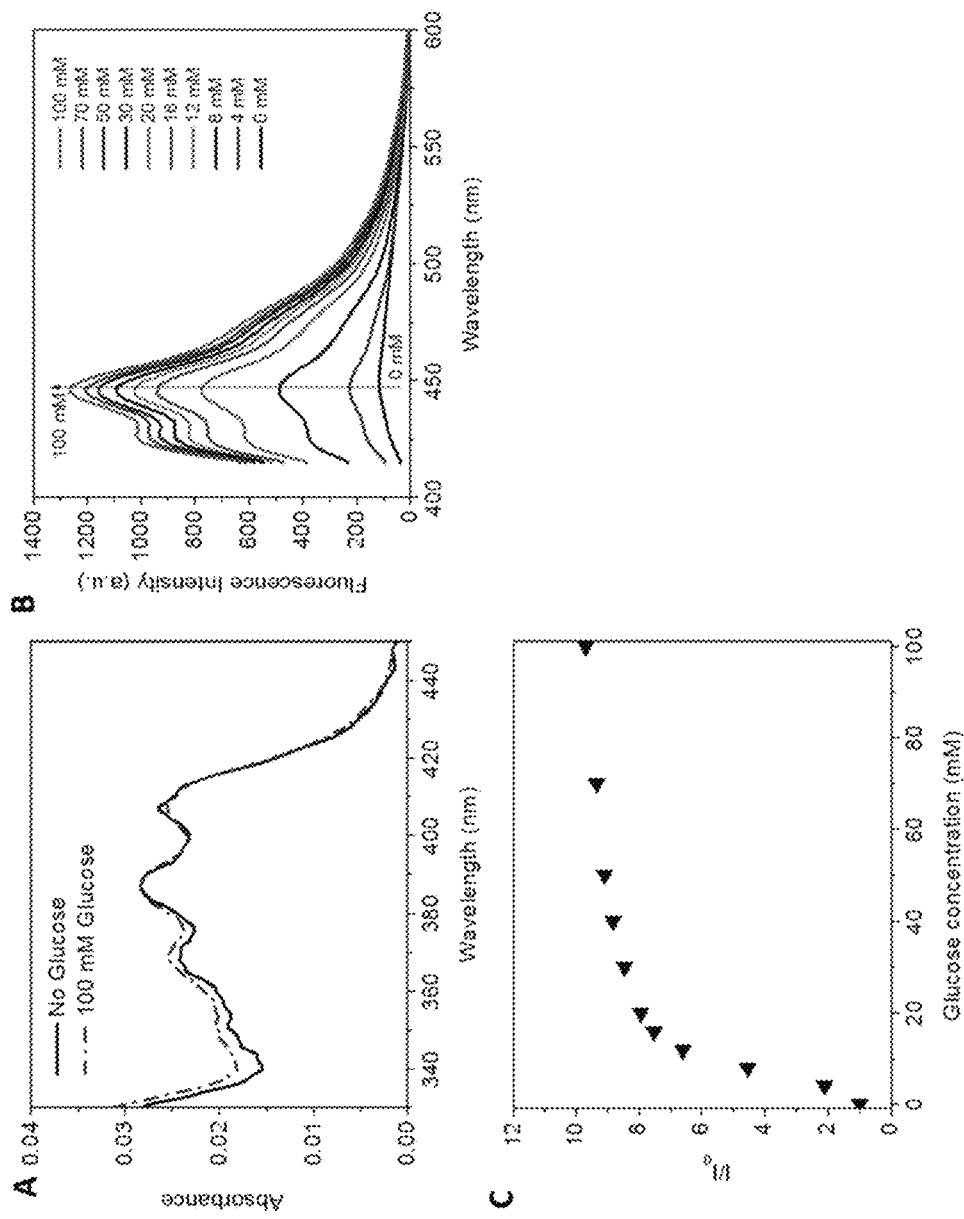
FIG. 3 shows responses of an optical fluorescence dual sensor according to an embodiment of the invention.

Five films (F1-F5) with variable weight ratios of PHEMA to PAM (Table 1) were prepared with a fixed 7.5% of PMAHA in the films. FIG. 3A shows the typical sensor responses of the film F5. The absorption spectra of the sensor has no changes before or after interactions with glucose (FIG. 3A). The emission intensity increases with increasing of glucose concentration (FIG. 3B), showing the sensing mechanism is due to photo-induced electron transfer (PET). A fluorescence intensity ratio at 445 nm was plotted in FIG. 3C. It could be found that the sensor film had a sensitive dynamic range to glucose from 1 mM to 30 mM, indicating the sensor is suitable for cultured cell glucose metabolism assay [46], as well as for blood glucose concentration monitoring for diabetes [47].

Figure 4:
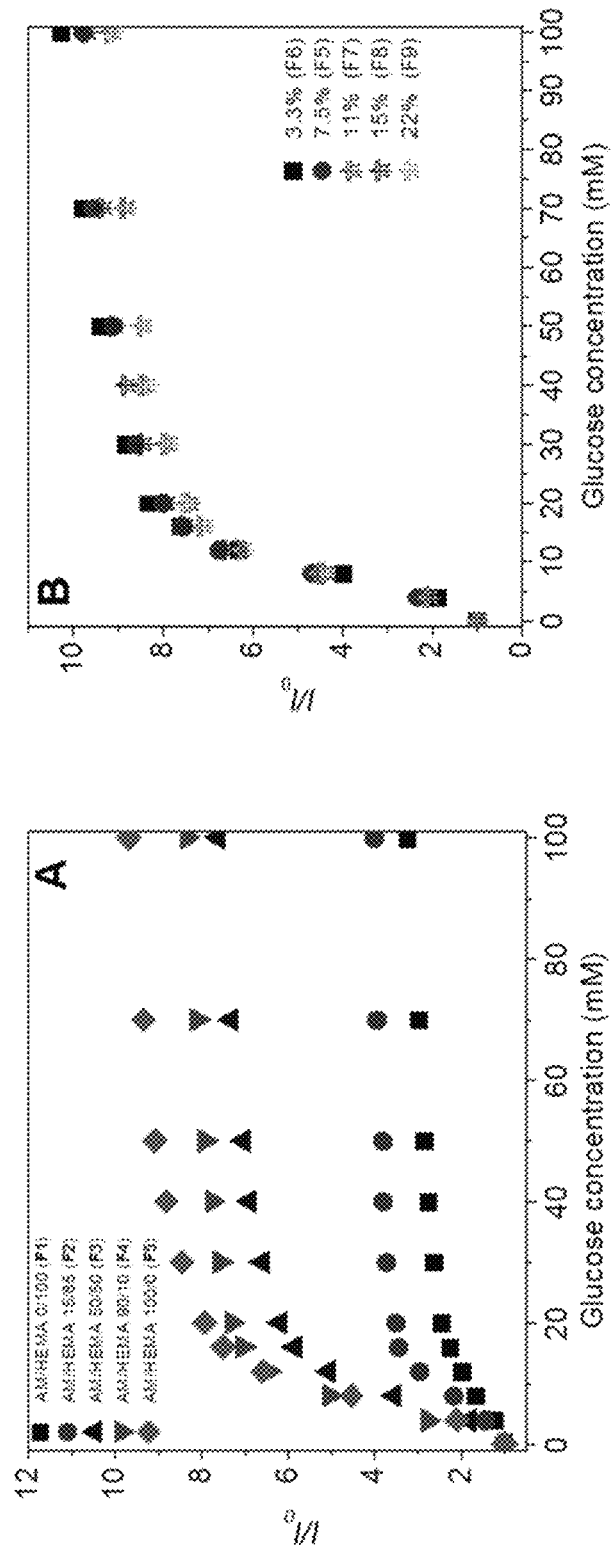
FIG. 4 shows the influence of matrices on glucose responses.

FIG. 4A shows the sensor responses of F1~F5 to glucose. It was found that PHEMA has a strong negative effect on the glucose response of sensing films. The films with more PHEMA have a lower sensitivity to glucose. Without PAM, the sensing film F had the sensitivity (1100 mM/10 mM) of 3.2-fold. The sensing film F5 showed the highest sensitivity (9.8-fold) (FIG. 3A and Table 1). Therefore, after the optimization, we chose the polyacrylamide (PAM) as the matrices for sensor film preparation.

Influences of MAHA on the Sensor Performance

Films F5-F9 were prepared using PAM as the matrices, while with different weight ratios of PMAHA. FIG. 4B shows the comparisons of the sensor performance. It was found that amounts of probe linker (MAHA), from 5% to 22%, did not show much effect on the sensitivities to glucose. Taking the sensitivity and quality of sensing films into account, the matrix compositions of sensing film F5 was selected as the only recipe for dual sensor preparation.

Evaluation of the Selectivity to Glucose

Figure 5:
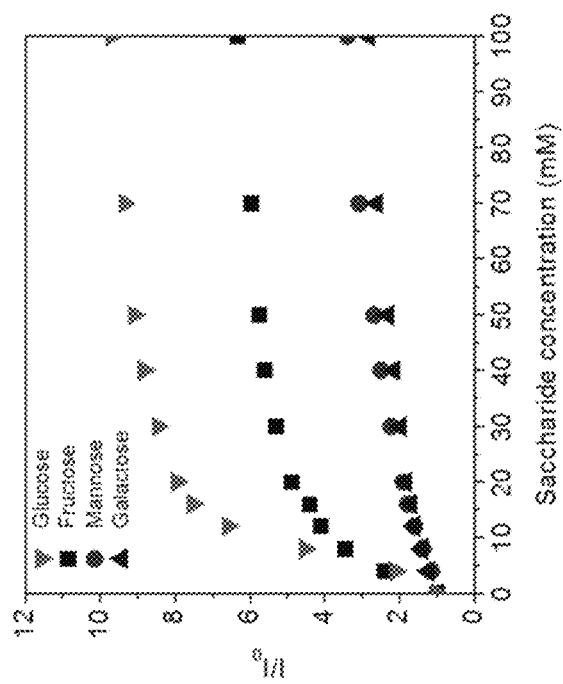
FIG. 5 evaluates the selectivity of a sensor according to an embodiment of the invention to different saccharides. $I_0$ is the intensity at 445 nm without any saccharides and I is the intensity at 445 nm with saccharide.

The selectivity of sensing film was studied by determining fluorescent response to different saccharides, i.e. glucose, fructose, mannose and galactose. As shown in FIG. 5, the sensing film has the highest selectivity to glucose.

pH Effect on the Glucose Thin Film Sensor

Figure 6:
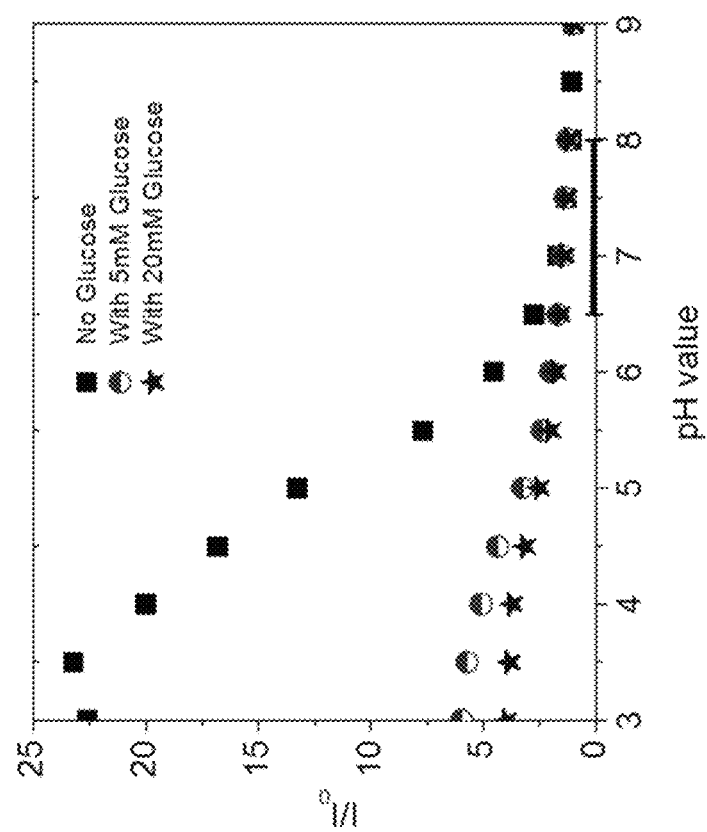
FIG. 6 shows the influence of pH on the response of a sensor according to an embodiment of the invention. $I_0$ is the intensity at 445 nm at pH 9 and I is the intensity at 445 nm at various pH.

Due to metabolites produced during cell metabolism, the pH of the cell environment changes in a narrow range [38, 48]. It is important to know if the change is going to affect the performance of sensing film. The sensing film F5 was titrated from pH3 to pH9 with or without glucose. As shown in FIG. 6, at the condition without glucose, the sensor suffered seriously from pH changes. But with the existence of 5 mM or 20 mM glucose in the media, fluorescent responses to pH decreased significantly, especially in the physiological pH range, i.e. from 6.5 to 8. The glucose sensor has almost no response to pH from pH 6.5 to 8, indicating, that the glucose sensor is applicable to analyze glucose in physiological conditions without the interferences by pH.

Dual Glucose-Oxygen Sensor

Figure 7:
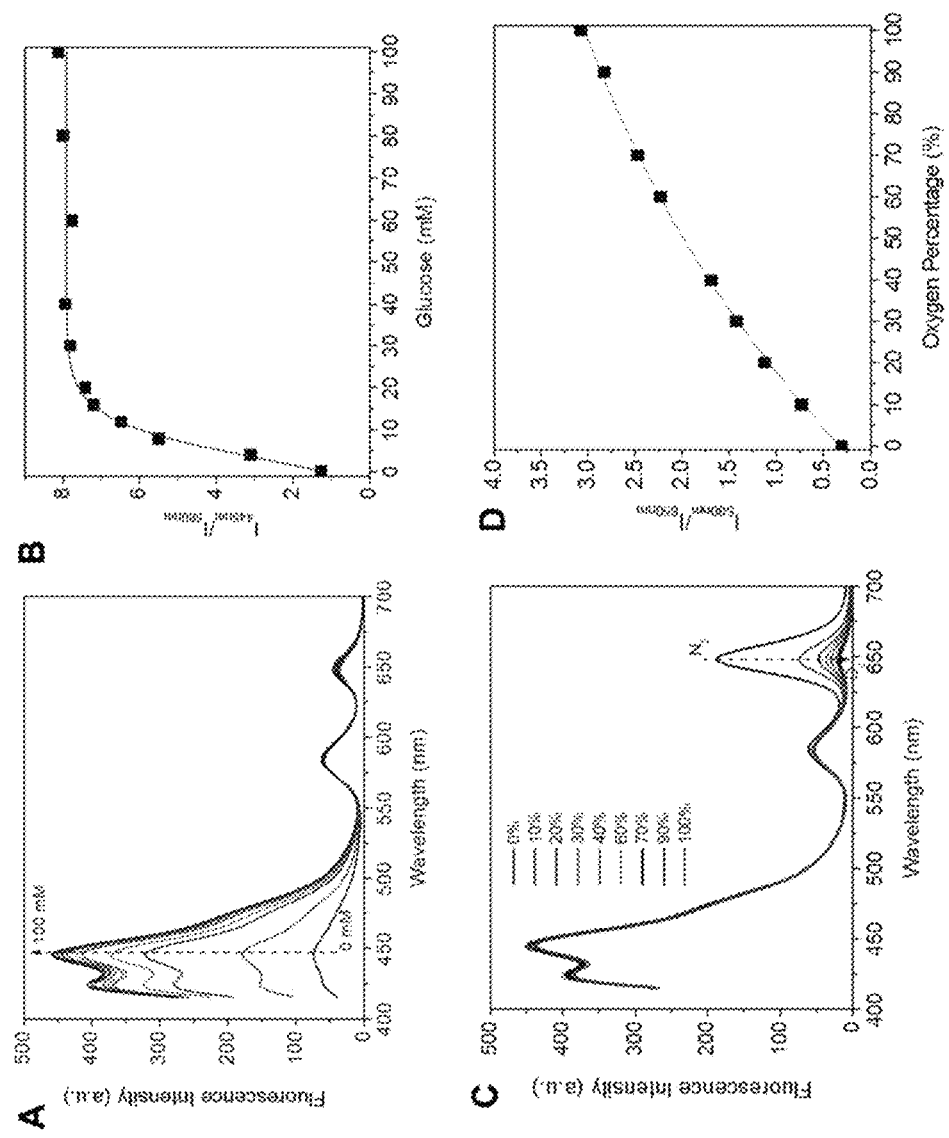
FIG. 7 shows responses of a dual sensor according to an embodiment of the invention to glucose (FIGS. 7A and B) and to oxygen (FIGS. 7C and D).

A dual sensor (film F10) was prepared by using a ratio of the matrix precursors of AM:MAHA:PEGDMA of 77.5:7.5:15. Weight ratios of OS, GHS-NS, and Rhod-MA in the matrix are of 0.32%:0.6%:0.1%. FIG. 7 shows the responses of the dual sensor to glucose and oxygen. It can be found that the internal built-in reference probe of Rhod-MA with an emission maximum at 580 nm and the oxygen probe with an emission maximum at 650 nm did not respond to glucose (FIG. 7A). Rhod-MA and GS did not respond to oxygen (FIG. 7C). This observation showed that the Rhod-MA is a suitable internal reference probe, enabling the application of the ratiometric approach for the glucose and oxygen concentration calculation. Further, there are no cross-talks between the oxygen probes and glucose probes. All of the probes can be excited efficiently using a single wavelength, simplifying the optical operational condition when used for bioanalysis. FIG. 7B shows the glucose response calculated using the ratiometric approach (I445/I580) of the dual sensor film. The sensor responds to glucose in a range of 1 to 20 mM, much narrower than the glucose sensors film of F5. This may be due to that the film F10 contains a greater amount of crosslinks, e.g. the oxygen probe molecules, to make the network tight, which most likely affected the glucose permeability in the films as well as the dynamic range to glucose. Other possibilities such as the fluorescence resonance energy transfer (FRET) among the three fluorophores in the thin films may also affect the sensor performance. FIG. 7D shows the Stern-Volmer plot of the dual sensor to oxygen using the ratiometric approach. The responses to oxygen are not linear, indicating the non-uniform distributions of the oxygen probes in the films and/or some possible FRET effects among the three fluorophores Application of the Dual Sensor Film to Monitor Extracellular Glucose and Oxygen Changes During Bacteria Growth Sugar concentration and dissolved oxygen are two important factors that affect microbial growth, and vice versa, consumption rates of sugar and oxygen reflect the physiological state of the microbial culture [48]. Many methods and tools have been developed to monitor the consumption rates of glucose and oxygen. For the glucose consumption assay, most commonly used assay methods include [U—$^{14}$C] glucose-labeling experiment [49], fluorescent glucose analog, 2-NBDG [50, 51] and other indirect methods like phosphorus-31 nuclear magnetic resonance ($^{31}$P-NMR) spectroscopy [52]. Well-trained and experienced operators are required to handle those radioactive materials. Glucose analogs, 2-NBDG, actually are metabolism inhibitors by which metabolic stresses are going to be produced during experiments. The results collected by these analogs most likely lack the ability to reflect the real cell metabolism level.

Figure 8:
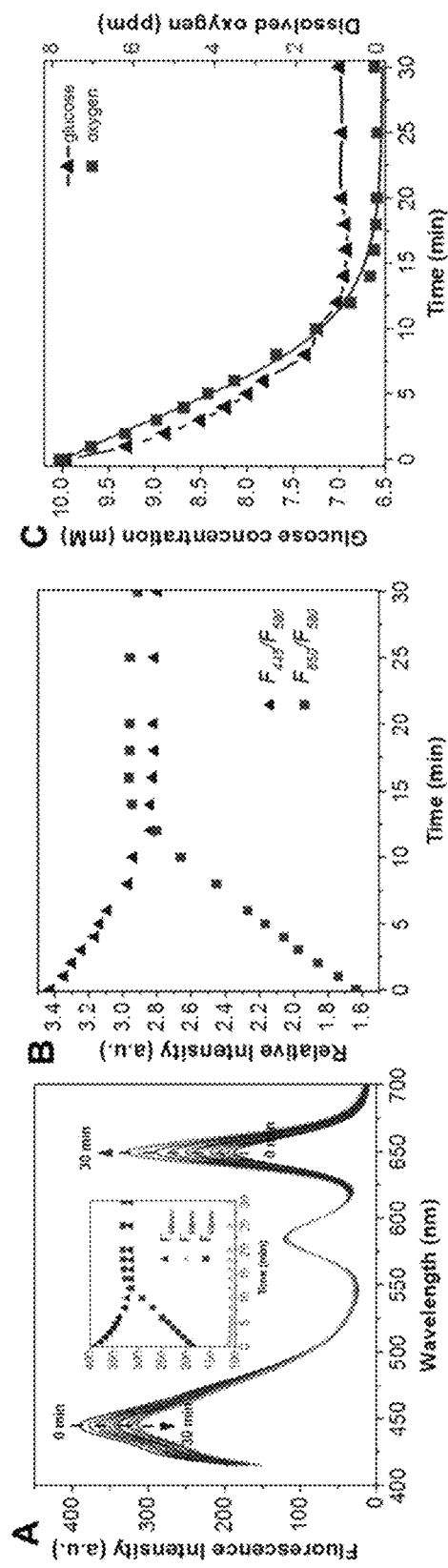
FIG. 8A shows emission spectral changes of a sensor according to an embodiment of the invention during the growth of B. subtilis (4×10⁷ cfu/mL).
FIG. 8B shows the time dependent glucose and oxygen concentrations and their changes during growth of B. subtilis.

The non-invasive dual glucose and oxygen sensor of the present disclosure were used to investigate the kinetic real-time cell metabolism. The capability of detecting changes of glucose and oxygen were tested with *E. coli* and *B. subtilis*. FIG. 8A shows the typical spectral changes during the cell growth of *B. subtilis* with a cell density of $4 \times 10^7$ cfu/mL. Because cells consume glucose and oxygen during growth and respiration, both the glucose and oxygen concentrations decrease, which will result in a decrease of the glucose sensor's intensity at 445 nm, while an increase of the oxygen sensor's intensity at 650 nm. According to the titration curve of the sensor using the ratiometric approach, the real-time concentrations of glucose and oxygen were calculated and plotted in FIG. 8B. It can be seen that at such a condition, oxygen was consumed completely by the bacteria at about 15 min. According to the time dependent concentrations, the "drawndown" rates of glucose and oxygen by *B. subtilis* in 10 min were determined as $6.92 \pm 0.45$ fmol $\text{min}^{-1}$ $\text{cfu}^{-1}$ and $0.49 \pm 0.05$ fmol $\text{min}^{-1}$ $\text{cfu}^{-1}$, respectively (Table 2).

TABLE 2

Glucose uptake and oxygen consumption rates by cells.

| | Cell density | Glucose (fmol $\text{min}^{-1}$ $\text{cell}^{-1}$) | Oxygen (fmol $\text{min}^{-1}$ $\text{cell}^{-1}$) |
|---|---|---|---|
| *E. coli* | $1 \times 10^8$ cfu $\text{mL}^{-1}$ | $0.66 \pm 0.02^a$ | $0.17 \pm 0.03^a$ |
| | | $0.28 \pm 0.03^b$ | $0.08 \pm 0.02^b$ |
| *B. subtilis* | $4 \times 10^7$ cfu $\text{mL}^{-1}$ | $6.92 \pm 0.45^a$ | $0.49 \pm 0.05^a$ |
| | | $2.51 \pm 0.03^b$ | $0.21 \pm 0.02^b$ |
| HeLa cells | $1 \times 10^6$ cells $\text{mL}^{-1}$ | $12.1 \pm 1.5^c$ | $1.98 \pm 0.3^c$ |
| J774 cells | $1 \times 10^6$ cells $\text{mL}^{-1}$ | $4.75 \pm 0.4^c$ | $1.59 \pm 0.2^c$ |

$^a$Average rate in 10 min.
$^b$Average rate in 30 min.
$^c$Average rate in 120 min.

FIG. 8C presents the kinetic curves demonstrating the uptake of glucose and consumption of oxygen by *E. coli* with the same optical density as *B. subtilis*, i.e. OD600=0.2. In this testing condition, the "drawdown" rates of glucose and oxygen by *E. coli* (JM109) in 10 min were determined to be $0.66 \pm 0.02$ fmol $\text{min}^{-1}$ $\text{cfu}^{-1}$ and $0.17 \pm 0.03$ fmol $\text{min}^{-1}$ $\text{cfu}^{-1}$ respectively (Table 2).

It is notable that the "drawdown" rates of glucose and oxygen depend on the time scale. The rates determined using a 30 min time scale are much slower than those determined in a 10 min time scale. The comparison was given in Table 2. For the same bacterial species, the observation of the time-depend oxygen and glucose consumption rates shows the advantage of the glucose-oxygen dual sensor as compared to other traditional approaches. The advantage is that the sensor of the present disclosure can monitor the real-time metabolism level of living organisms without invasion. That dynamic data may reflect the metabolism of cells at a specific proliferation stage or differentiation state.

Figure 9:
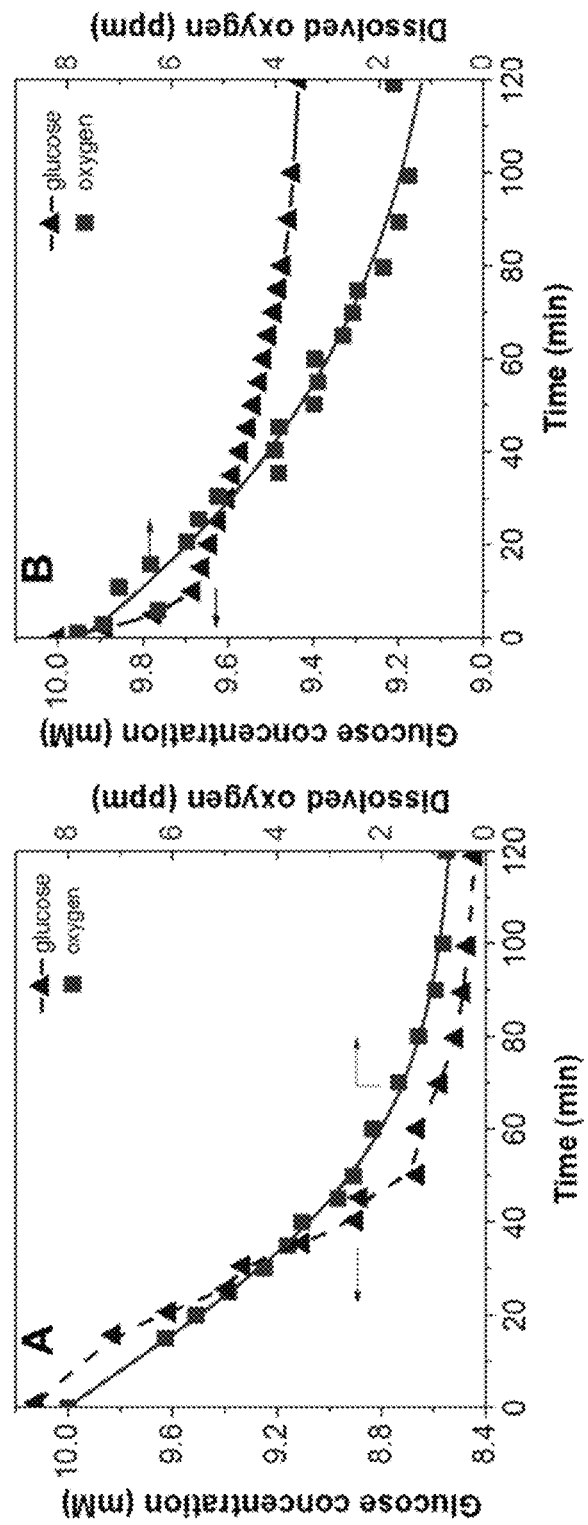
FIG. 9 shows glucose uptake and oxygen consumption assay by HeLa cells (A) and J774 cells (B) detected by a dual sensor according to an embodiment of the invention.

Application of Sensing Film F10 to Monitor the Consumption of Glucose and Oxygen for Mammalian Cells Two mammalian cell lines, murine macrophage cell line J774 and HeLa cells were applied to test the glucose uptake and oxygen consumption rates by the film F10 (FIG. 9). For both of the cell lines, under our experimental conditions, cells consumed oxygen completely within 2 hours. However, clear differences of their glucose uptakes were observed. At the same time point, HeLa cells consumed oxygen faster than J774 did. Using the 2 hour time scale, the oxygen consumption and glucose uptake rates were calculated and given in Table 2. Very similar oxygen consumption rates were determined, i.e. $1.98 \pm 0.3$ fmol $\text{min}^{-1}$ $\text{cell}^{-1}$ for HeLa cells and $1.59 \pm 0.2$ fmol $\text{min}^{-1}$ $\text{cell}^{-1}$ for J774 cells, while different glucose uptake rates were observed: $12.1 \pm 1.5$ fmol $\text{min}^{-1}$ $\text{cell}^{-1}$ for HeLa cells and $4.75 \pm 0.4$ fmol $\text{min}^{-1}$ $\text{cell}^{-1}$ for J774 cells (Table 2).

CONCLUSION

The influence of a polymer matrix on the glucose sensing performance was investigated. Results showed that polyacrylamide is a good matrix for glucose sensing. The dual glucose and oxygen sensor composed of three fluorophores, a red emitter as an oxygen probe, a yellow emitter as a built-in reference probe, which does not respond to either glucose or oxygen, and a blue emitter as the glucose probe. The three probes were chemically grafted in the polyacrylamide matrix. Because of an integration of the built-in reference probe with glucose and oxygen probes, the ratiometric approach was used to measure glucose and oxygen concentrations at biological environments. Results showed that the tricolor dual glucose and oxygen sensor is not only suitable for the determination of glucose and/or oxygen level at the set time point, but can also simultaneously monitor in real-time the glucose and oxygen concentration changes/consumptions by bacteria and mammalian cells. The sensor's capability of monitoring dynamic changes of oxygen and glucose at real-time provides researchers more information than traditional techniques.

The following cited references are incorporated by reference in their entireties:

[1] Vander Heiden M G, Cantley L C, Thompson C B. Understanding the Warburg effect: the metabolic requirements of cell proliferation. Science 2009; 324:1029-1033.

[2] Yamamoto N, Ueda M, Sato T, Kawasaki K, Sawada K, Kawabata K, Ashida H. Measurement of glucose uptake in cultured cells. Curr Protoc Pharmacol 2011; p 12.14.1-12.14.22.

[3] Kaelin W G Jr, Thompson C B. Q&A: Cancer: clues from cell metabolism. Nature 2010; 465: 562-564.

[4] DeBerardinis R J, Thompson C B. Cellular metabolism and disease: what do metabolic outliers teach us? Cell 2012:148:1132-1144.

[5] Gatenby R A, Gillies R J. Why do cancers have high aerobic glycolysis? Nat Rev Cancer 2004, 4:891-899.

[6] Muñoz-Pinedo C, El Mjiyad N, Ricci J E. Cancer metabolism: current perspectives and future directions. Cell Death Dis 2012; 3:e248.

[7] Griffin J L, Shockcor J P. Metabolic profiles of cancer cells. Nat Rev Cancer 2004; 4:551-561.

[8] Denkert C, Budczies J, Kind T, Weichert W, Tablack P, Sehouli J, Et al. Mass spectrometry-based metabolic profiling reveals different metabolites patterns in invasive ovarian carcinomas and ovarian borderline tumors. Cancer Res 2006; 66:10795-10804.

[9] Glunde K, Artemov D, Penet M F, Jacobs M A, Bhujwalla Z M. Magnetic resonance spectroscopy in metabolic and molecular imaging, and diagnosis of cancer. Chem. Rev 2010:110:3043-3059.

[10] Roupe K A, Helms G L, Halls S C. Yáñez J A, Davies N M. Preparative enzymatic synthesis and HPLC analysis of rhapontigenin: application to metabolism, pharmacokinetics and anti-cancer studies. J. Pharm. Pharmaceut Sci 2005; 8:374-86.

[11] Bas Teusink, Jasper A. Diderich, Hans V. Westerhoff, Karel van Dam, and Micheal C. Walsh. Intracellular glucose concentration in depressed yeast cells consuming glucose is high enough to reduce the glucose transport rate by 50%. Journal of Bacteriology 1998, 180: 556-62.

[12] Vander Heiden M G, Plas D R, Rathmell J C, Fox C J, Harris M H, Thompson C B. Growth factors can influence cell growth and survival through effects on glucose metabolism. Mol Cell Biol. 2001; 21:5899-912.

[13] Dringen R, Hamprecht B. Inhibition by 2-deoxyglucose and 1,5-gluconolactone of glycogen mobilization in astroglia-rich primary cultures. J Neurochem 1993; 60:1498-1504.

[14] Brauer H A, Makowski L, Hoadley K A, Casbas-Hernandez P, Lang L J. Romàn-Pèrez E. et al. Impact of tumor microenvironment and epithelial phenotypes on metabolism in breast cancer. Clin Cancer Res 2013; 19:571-585.

[15] Fowler J S, Ido T. Initial and subsequent approach for the synthesis of 18FDG. Semin Nucl Med. 2002; 32:6-12.

[16] Pritchard K I, Julian J A, Holloway C M, McCready D, Gulenchyn K Y, George R, Et al. Prospective study of 2-[$^{18}$F]fluorodeoxyglucose positron emission tomography in the assessment of regional nodal spread of disease in patients with breast cancer: an Ontario clinical oncology group study. J Clin Oncol 2012; 30:1274-1249.

[17] Ramírez-Peinado S, Alcázar-Limones F, Lagares-Tena L, El Mjiyad N, Caro-Maldonado A, Tirado O M, Et al. 2-deoxyglucose induces Noxa-dependent apoptosis in alveolar rhabdomyosarcoma. Cancer Res. 2012; 71:6796-6806.

[18] Heller A, Feldman B., Electrochemical glucose sensors and their applications in diabetes management, Chem. Rev., 2008; 108:2482-2505.

[19] Pringsheim E, Terpetsching E, Piletsky S A, and Wolfbeis O S. A polyaniline with near-infrared optical response to saccharide. Adv Mater 1999; 11:865-868.

[20] Pickup J C, Hussain F, Evans N D, Rolinski O J, Birch D J, Fluorescence-based glucose sensors. Biosens Bioelectron 2005; 20:2555-2565.

[21] Li S, Davis E N, Anderson J, Lin Q. Wang Q. Development of boronic acid grafted random copolymer sensing fluid for continuous glucose monitoring, Biomacromolecules 2009; 10:113-118.

[22] Steiner M S, Duerkop A, Wolfbeis O S. Optical methods for sensing glucose. Chem Soc Rev 2011; 40:4805-4839.

[23] Mader H S, Wolfbeis O S. Boronic acid based probes for microdetermination of saccharides and glycosylated biomolecules. Microchim Acta 2008:162:1-34.

[24] Fang H, Kaur G, Wang B. Progress in Boronic acid-based fluorescent glucose sensors. J Fluoresc 2004; 14:481-489.

[25] James T D, Sandanayake K R A S, Iguchi R, and Shinkai S. Novel saccharide-photoinduced electron transfer sensors based on the interaction of boronic acid and amine. J Am Chem Soc 1995; 117:898289-97.

[26] Kawanishi T, Romey M A, Zhu P C, Holody M Z, Shinkai S. A study of boronic acid based fluorescent glucose sensors. J Fluoresc 2004; 14:499-512.

[27] Lorand J P, and Edwards J O. Polyol complexes and structure of the benzeneboronate ion, J Org Chem 1959: 24:769-774.

[28] Shibata H, Heo Y J, Okitsu T, Matsunaga Y, Kawanishi T, Takeuchi S. Injectable hydrogel microbeads for fluorescence-based in vivo continuous glucose monitoring, Proc Natl Acad Sci USA. 2010; 107:17894-17898.

[29] Heo Y J, Shibata H, Okitsu T, Kawanishi T. Takeuchi S. Long-term in vivo glucose monitoring using fluorescent hydrogel fibers, Proc Natl Acad Sci USA. 2011; 108:13399-13403.

[30] Tian Y, Shumway B R, Meldrum D R. A new crosslinkable oxygen sensor covalently bonded into poly(2-hydroxyethyl methacrylate)-co-polyacrylamide thin film for dissolved oxygen sensing. Chem Mater, 2010:22: 2069-2078.

[31] Xu H, Aylott J W, Kopelman R, Miller T J, Philbert M A. A real-time ratiometric method for the determination of molecular oxygen inside living cells using sol-gel-based spherical optical nanosensors with applications to rat C6 glioma. Anal. Chem., 2001:73:4124-4133.

[32] Kermis, H R, Kostov, Y, Harms, P, Rao, G. Dual Excitation Ratiometric Fluorescent pH Sensor for Non-invasive Bioprocess Monitoring: Development and Application. Biotechnol. Prog., 2002: 18:1047-1053.

[33] Schaeferling M, Duerkop, A. Intrinsically referenced Fluorimetric Sensing and Detecting Schemes: Methods, Advantages and Applications. Springer Ser. Fluoresc., 2008:5:373-414.

[34] Lu H, Jin Y, Tian Y, Zhang W, Holl M R, Meldrum D R. New ratiometric optical oxygen and pH dual sensors with three emission colors for measuring photosynthetic activity in cyanobacteria. J Mater Chem 2011: 21:19293-19301.

[35] Zhou X, Su F, Lu H, Senechal-Willis P, Tian Y, Johnson R H, Meldrum D R. An FRET-based ratiometric chemosensor for in vitro cellular fluorescence analyses of pH. Biomaterials 2012: 33: 171-180.

[36] Best Q A, Xu R, McCarroll M E, Wang L, Dyer D J. Design and investigation of a series of rhodamine-based fluorescent probes for optical measurements of pH. Org Lett 2010; 12:3219-3221.

[37] Chen B K, Lo S H, and Lee S F. Temperature responsive methacrylamide polymers with antibacterial activity. Chinese J Polym Sci 2010; 28:607-613.

[38] Tian, Y, Su, F, Weber, W, Nandakumar, V, Shumway, B R, Jin, Y, Zhou, X, Holl, M R, Johnson, R H, Meldrum, D R. A series of naphthalimide derivatives as intra and extracellular pH sensors. Biomaterials 2010:31:7400-22.

[39] Mallette M F. In: Norris J R, Ribbons D W, editors. Evaluation of growth by physical and chemical means in methods in microbiology. Vol 1. London: Academic Press; 1969. P. 521-66.

[40] Haas M, Beyer D, Gahlmann R, and Freiberg C. YkrB is the main peptide deformylase in Bacillus subtilis, a eubacterium containing two functional peptide deformylases. Microbiology 2001; 147:1783-1791.

[41] Jelenc P C. Rapid purification of highly active ribosomes from Escherichia coli. Anal. Biochem. 1980; 105: 369-374.

[42] Guo P, Zhang L, Zhang H, Feng Y, and Jing G. Domain II plays a crucial role in the function of ribosome recycling factor. Biochem J 2006:393:767-777.

[43] Tian, Y, Shumway, B R, Gao, W, Youngbull, C, Holl. M R, Johnson, R H, et al. Influence of Matrices on Oxygen Sensing of Three Sensing Films with Chemically Conjugated Platinum Porphyrin Probes and Preliminary Application for Monitoring of Oxygen Consumption of Escherichia coli (E. coli). Sens Actuators B Chem 2010; 150:579-587.

[44] Formasiero F, Krull F, Prausnitz J M, Radke C J. Biomaterials, Steady-State Diffusion of Water through Soft-Contact-Lens Materials, 2005:26:5704-5716.

[45] Wang Y, Tan G, Zhang S, Guang Y. Influence of water states in hydrogels on the transmissibility and permeability of oxygen in contact lens materials. Appl. Surf. Sci., 2008, 255, 604-606.

[46] Blaker G J, Birch J R, and Pirt S J. The glucose, insulin and glutamine requirements of suspension cultures of HeLa cells in a defined culture medium. J Cell Sci 1971; 9:529-537.

[47] Daly M E, Vale C, Walker M, Littlefield A, Alberti K G M M, and Mathers J C. Acute effects on insulin sensitivity and diurnal metabolic profiles of a high-sucrose compared with a high-starch diet. Am J Clin Nutr 1998:67:1186-96.

[48] Monod J. The growth of bacterial cultures. Annu Rev Microbiol 1949; 3:371-394.

[49] Briczinski E P, Phillips A T, and Roberts R F. Transport of Glucose by bifidobacterium animalis subsp. Lactis occurs via facilitated diffusion. Appl. Environ. Microbiol. 2008; 74:6941-48.

[50] Yoshioka K, Takahashi H, Homma T, Saito M, Oh K-B, Nemoto Yasushi, and Matsuoka H. A novel fluorescent derivative of glucose applicable to the assessment of glucose uptake activity of Escherichia coli. Biochim. Biophys. Acta. 1996; 1289:5-9.

[51] Naterajan A, Srienc F. Glucose uptake rates of single E. coli cells grown in glucose-limited chemostat cultures. J. Microbiol. Methods. 2000; 42:87-96.

[52] Chen R, Yap W M G J, Postma P W, and Bailey J E. Comparative studies of Escherichia coli strains using different glucose uptake systems: metabolism and energetics. Biotechnol. Bioeng. 1997; 56: 583-90.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention.

What is claimed is:

1. An optical fluorescence sensor comprising:
a probe for sensing glucose, an intra-reference probe and a matrix, wherein
the probe for sensing glucose is prepared from a compound having formula I:

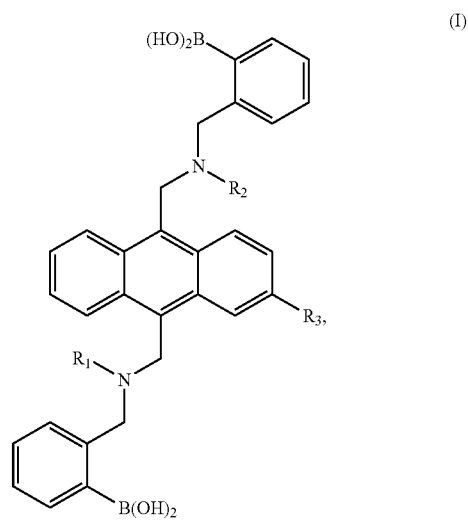

wherein $R_1$ and $R_2$ can be the same or different and are $C_nH_{2n+1}$, where n is an integer selected from the group consisting of 0, 1, 2, 3, 4, 5, 6, 7 and 8;
$R_3$ is selected from the group consisting of $(CH_2)_nC(O)OH$, $O(CH_2)_nC(O)OH$, $NH(CH_2)_nC(O)OH$, $(CH_2)_nC(O)OR_4$, $O(CH_2)_nC(O)OR_4$, $NH(CH_2)_nC(O)OR_4$, $(CH_2)_nC(O)NH(CH_2)_nNH-A$, $O(CH_2)_nC(O)NH(CH_2)_nNH-A$, $NH(CH_2)_nC(O)NH(CH_2)_nNH-A$, $(CH_2)_nC(O)O(CH_2)_nNH-A$, $O(CH_2)_nC(O)O(CH_2)_nNH-A$, $NH(CH_2)_nC(O)O(CH_2)_nNH-A$, $(CH_2)_nC(O)NH(CH_2)_nNH-M'A$, $O(CH_2)_nC(O)NH(CH_2)_nNH-M'A$, $NH(CH_2)_nC(O)NH(CH_2)_nNH-M'A$, $(CH_2)_nC(O)O(CH_2)_nNH-M'A$, $O(CH_2)_nC(O)O(CH_2)_nNH-M'A$, $NH(CH_2)_nC(O)O(CH_2)_nNH-M'A$, $(CH_2)_nC(O)NH(CH_2)_nNH-VA$, $O(CH_2)_nC(O)NH(CH_2)_nNH-VA$, $NH(CH_2)_nC(O)NH(CH_2)_nNH-VA$, $(CH_2)_nC(O)O(CH_2)_nNH-VA$, $O(CH_2)_nC(O)O(CH_2)_nNH-VA$, and $NH(CH_2)_nC(O)O(CH_2)_nNH-VA$;
n is an integer selected from the group of consisting of 0, 1, 2, 3, 4, 5, 6, 7, 8, 9, 10, 11 and 12;
$R_4$ is an activating group;

M'A is

A is

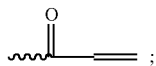

and
VA is

the intra-reference probe is prepared from a compound having formula III:

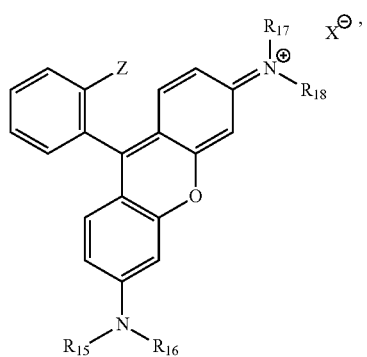

wherein $R_{15}$, $R_{16}$, $R_{17}$, and $R_{18}$ can be the same or different and are $C_nH_{2n+1}$, where n is an integer selected from the group consisting of 1, 2, 3, 4, 5, 6, 7 and 8;

X is an anion; and

Z is selected from the group consisting of: $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, and $CH_2(OCH_2CH_2)_rOVA$;

p is an integer selected from the group consisting of 1, 2, 3, 4, 5, 6, 7, 8, 9, 10, 11 and 12;

q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and r is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and the matrix is prepared from a monomer selected from the group consisting of acrylamide, N-(6-aminohexyl) methacrylamide, poly(ethylene glycol) dimethacrylate, methoxy-poly(ethylene glycol) methacrylate, 2-hydroxyethyl methacrylate and combinations thereof wherein the probe for sensing glucose and the intra-reference probe are attached to or immobilized in the matrix.

2. The optical fluorescence sensor according to claim 1, wherein the compound of formula I is:

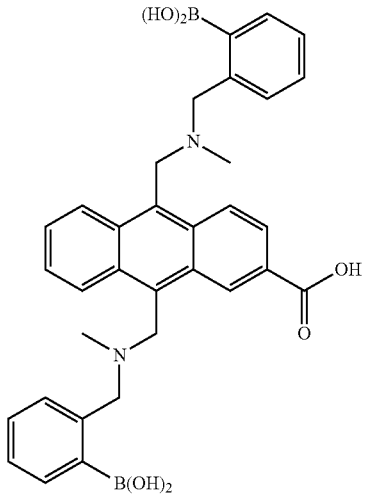 [SMILES: CN(Cc1ccccc1B(O)O)Cc1c2ccccc2c(CN(C)Cc2ccccc2B(O)O)c2cc(C(=O)O)ccc12]

or an activated ester thereof.

3. The optical fluorescence sensor according to claim 1, wherein the compound of formula III is:

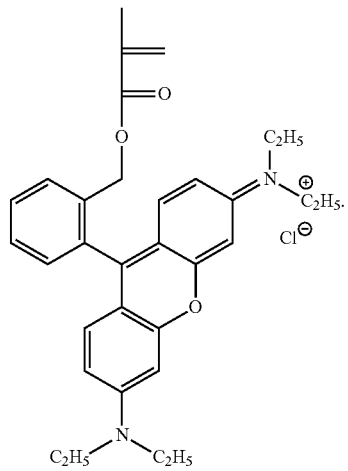

4. An optical fluorescence dual sensor comprising:
a probe for sensing glucose, a probe for sensing oxygen, an intra-reference probe and a matrix, wherein the probe for sensing glucose is prepared from a compound having formula I:

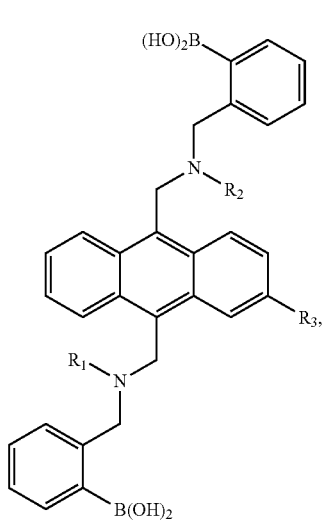

(I)

wherein $R_1$ and $R_2$ can be the same or different and are $C_nH_{2n+1}$, where n is an integer selected from the group consisting of 0, 1, 2, 3, 4, 5, 6, 7 and 8;

$R_3$ is selected from the group consisting of $(CH_2)_mC(O)OH$, $O(CH_2)_mC(O)OH$, $NH(CH_2)_mC(O)OH$, $(CH_2)_mC(O)OR_4$, $O(CH_2)_mC(O)OR_4$, $NH(CH_2)_mC(O)OR_4$, $(CH_2)_mC(O)NH(CH_2)_mNH-A$, $O(CH_2)_mC(O)NH(CH_2)_mNH-A$, $NH(CH_2)_mC(O)NH(CH_2)_mNH-A$, $(CH_2)_mC(O)O(CH_2)_mNH-A$, $O(CH_2)_mC(O)O(CH_2)_mNH-A$, $NH(CH_2)_mC(O)O(CH_2)_mNH-A$ $(CH_2)_mC(O)NH(CH_2)_mNH-M'A$, $O(CH_2)_mC(O)NH(CH_2)_mNH-M'A$, $NH(CH_2)_mC(O)NH(CH_2)_mNH-M'A$, $(CH_2)_mC(O)O(CH_2)_mNH-M'A$, $O(CH_2)_mC(O)O(CH_2)_mNH-M'A$, $NH(CH_2)_mC(O)O(CH_2)_mNH-M'A$, $(CH_2)_mC(O)NH(CH_2)_mNH-VA$, $O(CH_2)_mC(O)NH(CH_2)_mNH-VA$, $NH(CH_2)_mC(O)NH(CH_2)_mNH-VA$, $(CH_2)_mC(O)O(CH_2)_mNH-VA$, $O(CH_2)_mC(O)O(CH_2)_mNH-VA$, and $NH(CH_2)_mC(O)O(CH_2)_mNH-VA$;

m is an integer selected from the group of consisting of 0, 1, 2, 3, 4, 5, 6, 7, 8, 9, 10, 11 and 12;

$R_4$ is an activating group;

M'A is

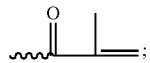

A is

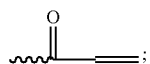

and

VA is

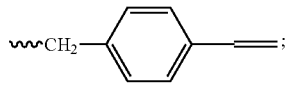

the probe for sensing oxygen is prepared from a compound having formula II:

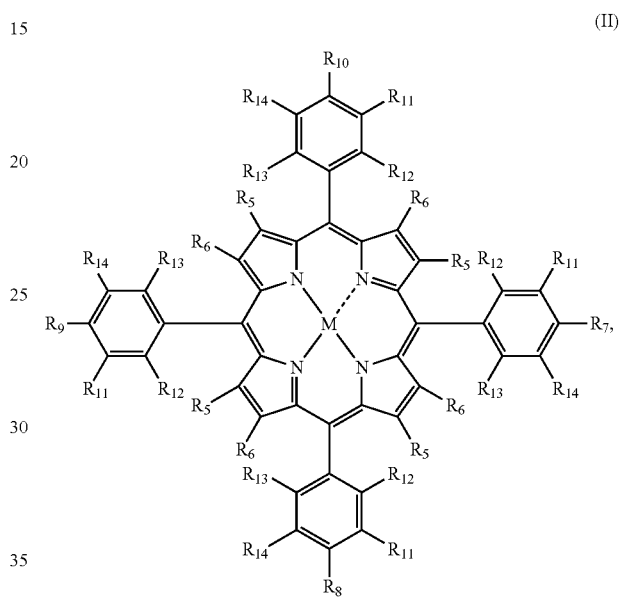

(II)

wherein M is selected from Pt or Pd;

$R_{11}$ and $R_{12}$ can be the same or different and are independently selected from the group consisting of H, F, Cl, Br, I, $CH_3$, $OCH_3$ and $OC_2H_5$;

$R_{13}$ and $R_{14}$ can be the same or different and are independently selected from the group consisting of H, F, Cl, Br, I, $CH_3$, $OCH_3$ and $OC_2H_5$;

$R_5$ and $R_6$ can be the same or different and are independently selected from the group consisting of H, F, Cl, Br, I, $CH_3$, $OCH_3$ and $OC_2H_5$;

$R_7$, $R_8$, $R_9$ and $R_{10}$ can be the same or different and are independently selected from the group consisting of $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, and $NH(CH_2CH_2O)_qVA$, where p is an integer selected from the group of consisting of 2, 3, 4, 5, 6, 7, 8, 9, 10, 11 and 12;

q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150;

the intra-reference probe is prepared from a compound having formula III:

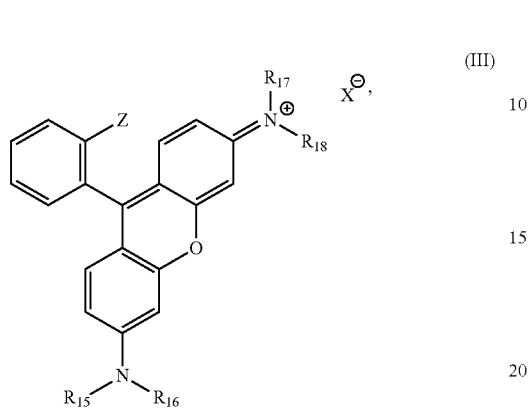

wherein $R_{15}$, $R_{16}$, $R_{17}$, and $R_{18}$ can be the same or different and are $C_nH_{2n+1}$, where n is an integer selected from the group consisting of 1, 2, 3, 4, 5, 6, 7 and 8;

X is an anion; and

Z is selected from the group consisting of: $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, and $CH_2(OCH_2CH_2)_rOVA$;

p is an integer selected from the group of consisting of 1, 2, 3, 4, 5, 6, 7, 8, 9, 10, 11 and 12;

q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and r is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and the matrix comprising is prepared from a polymer monomer selected from the group consisting of acrylamide, 6-aminohexyl methacrylamide, and poly(ethylene glycol) dimethacrylate, methoxy-poly(ethylene glycol) methacrylate, 2-hydroxyethyl methacrylate and combinations thereof;

wherein the probe for sensing glucose, the probe for sensing oxygen and the intra-reference probe are attached to or immobilized in the matrix.

5. The optical fluorescence dual sensor according to claim 4, wherein the compound of formula I is:

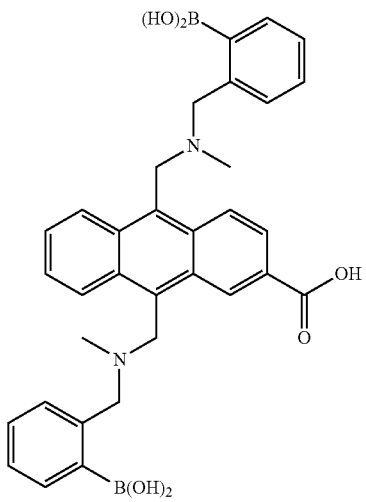 [SMILES: CN(Cc1ccccc1B(O)O)Cc1c2ccccc2c(CN(C)Cc2ccccc2B(O)O)c2cc(C(=O)O)ccc12]

or an activated ester thereof.

6. The optical fluorescence dual sensor according to claim 4, wherein the compound of formula II is:

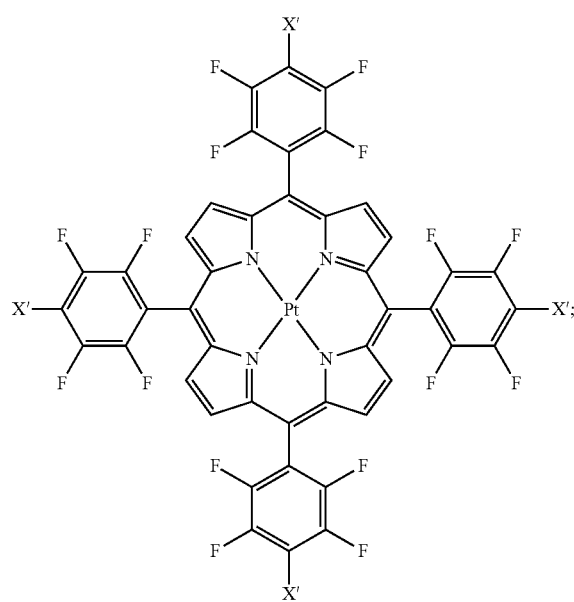

wherein X' is

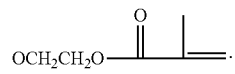

7. The optical fluorescence dual sensor according to claim 4, wherein the compound of formula III is:

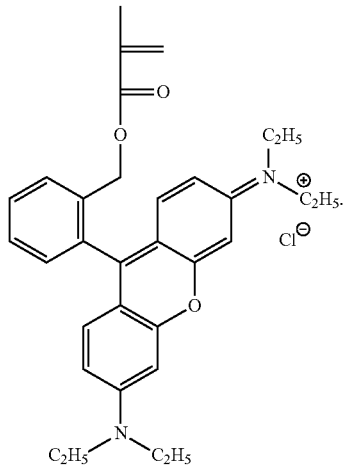

8. A method of preparing an optical fluorescence sensor comprising the steps of:
(a) copolymerizing an intra-reference probe, with 2-hydroxyethyl methacrylate, N-(6-aminohexyl) methacrylamide, and acrylamide onto a modified substrate; and
(b) attaching or immobilizing a probe for sensing glucose onto the substrate;

wherein the probe for sensing glucose has formula I:

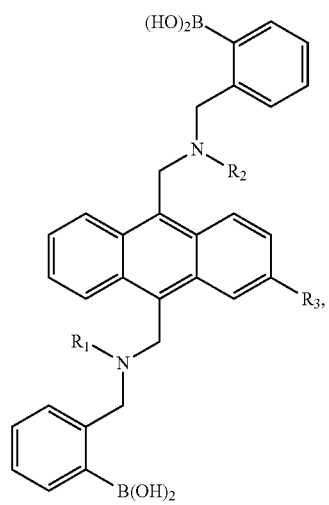

wherein $R_1$ and $R_2$ can be the same or different and are $C_nH_{2n+1}$, where n is an integer selected from the group consisting of 0, 1, 2, 3, 4, 5, 6, 7 and 8;

$R_3$ is selected from the group consisting of $(CH_2)_nC(O)OH$, $O(CH_2)_nC(O)OH$, $NH(CH_2)_nC(O)OH$, $(CH_2)_nC(O)OR_4$, $O(CH_2)_nC(O)OR_4$, $NH(CH_2)_nC(O)OR_4$, $(CH_2)_nC(O)NH(CH_2)_nNH-A$, $O(CH_2)_nC(O)NH(CH_2)_nNH-A$, $NH(CH_2)_nC(O)NH(CH_2)_nNH-A$, $(CH_2)_nC(O)O(CH_2)_nNH-A$, $O(CH_2)_nC(O)O(CH_2)_nNH-A$, $NH(CH_2)_nC(O)O(CH_2)_nNH-A$, $(CH_2)_nC(O)NH(CH_2)_nNH-M'A$, $O(CH_2)_nC(O)NH(CH_2)_nNH-M'A$, $NH(CH_2)_nC(O)NH(CH_2)_nNH-M'A$, $(CH_2)_nC(O)O(CH_2)_nNH-M'A$, $O(CH_2)_nC(O)O(CH_2)_nNH-M'A$, $NH(CH_2)_nC(O)O(CH_2)_nNH-M'A$, $(CH_2)_nC(O)NH(CH_2)_nNH-VA$, $O(CH_2)_nC(O)NH(CH_2)_nNH-VA$, $NH(CH_2)_nC(O)NH(CH_2)_nNH-VA$, $(CH_2)_nC(O)O(CH_2)_nNH-VA$, $O(CH_2)_nC(O)O(CH_2)_nNH-VA$, and $NH(CH_2)_nC(O)O(CH_2)_nNH-VA$;

n is an integer selected from the group consisting of 0, 1, 2, 3, 4, 5, 6, 7, 8, 9, 10, 11 and 12;

$R_4$ is an activating group;

M'A is

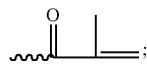

A is

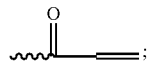

and
VA is

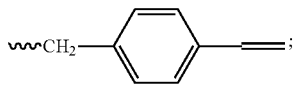

and the intra-reference probe has formula III:

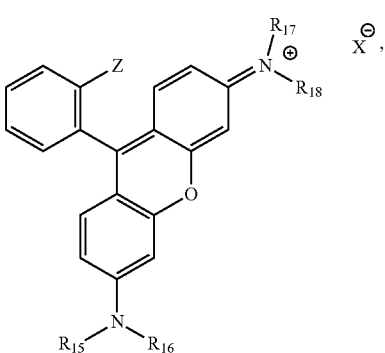

wherein $R_{15}$, $R_{16}$, $R_{17}$, and $R_{18}$ can be the same or different and are $C_nH_{2n+1}$, where n is an integer selected from the group consisting of 1, 2, 3, 4, 5, 6, 7 and 8;

X is an anion; and

Z is selected from the group consisting of: $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, and $CH_2(OCH_2CH_2)_rOVA$; and p is an integer selected from the group consisting of 1, 2, 3, 4, 5, 6, 7, 8, 9, 10, 11 and 12;

q is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and r is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

9. The method according to claim 8, wherein copolymerizing the intra-reference probe, with 2-hydroxyethyl methacrylate, N-(6-aminohexyl) methacrylamide, and acrylamide forms poly(2-hydroxyethyl methacrylate), poly(N-(6-aminohexyl) methacrylamide), poly(acrylamide), poly(2-hydroxyethyl methacrylate)-co-polyacrylamide-co-poly(N-(6-aminohexyl) methacrylamide) and their composites with the polymerized intra-reference probe.

10. A method of preparing an optical fluorescence sensor comprising the step of:

copolymerizing a probe for sensing glucose and an intra-reference probe, with 2-hydroxyethyl methacrylate, N-(6-aminohexyl) methacrylamide, and acrylamide onto a modified substrate;

wherein the probe for sensing glucose has formula I:

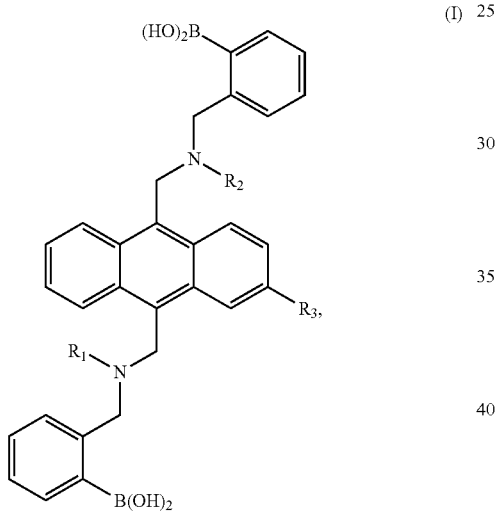

(I)

wherein $R_1$ and $R_2$ can be the same or different and are $C_nH_{2n+1}$, where n is an integer selected from the group consisting of 0, 1, 2, 3, 4, 5, 6, 7 and 8;

$R_3$ is selected from the group consisting of $(CH_2)_nC(O)OH$, $O(CH_2)_nC(O)OH$, $NH(CH_2)_nC(O)OH$, $(CH_2)_nC(O)OR_4$, $O(CH_2)_nC(O)OR_4$, $NH(CH_2)_nC(O)OR_4$, $(CH_2)_nC(O)NH(CH_2)_nNH-A$, $O(CH_2)_nC(O)NH(CH_2)_nNH-A$, $NH(CH_2)_nC(O)NH(CH_2)_nNH-A$, $(CH_2)_nC(O)O(CH_2)_nNH-A$, $O(CH_2)_nC(O)(CH_2)_nNH-A$, $NH(CH_2)_nC(O)(CH_2)_nNH-A$, $(CH_2)_nC(O)NH(CH_2)_nNH-M'A$, $O(CH_2)_nC(O)NH(CH_2)_nNH-M'A$, $NH(CH_2)_nC(O)NH(CH_2)_nNH-M'A$, $(CH_2)_nC(O)O(CH_2)_nNH-M'A$, $O(CH_2)_nC(O)O(CH_2)_nNH-M'A$, $NH(CH_2)_nC(O)O(CH_2)_nNH-M'A$, $(CH_2)_nC(O)NH(CH_2)_nNH-VA$, $O(CH_2)_nC(O)NH(CH_2)_nNH-VA$, $NH(CH_2)_nC(O)NH(CH_2)_nNH-VA$, $(CH_2)_nC(O)O(CH_2)_nNH-VA$, $O(CH_2)_nC(O)O(CH_2)_nNH-VA$, and $NH(CH_2)_nC(O)O(CH_2)_nNH-VA$;

n is an integer selected from the group consisting of 0, 1, 2, 3, 4, 5, 6, 7, 8, 9, 10, 11 and 12;

$R_4$ is an activating group;

M'A is

A is

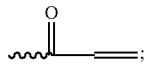

and

VA is

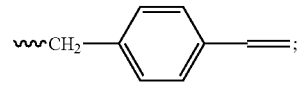

and the intra-reference probe has formula III:

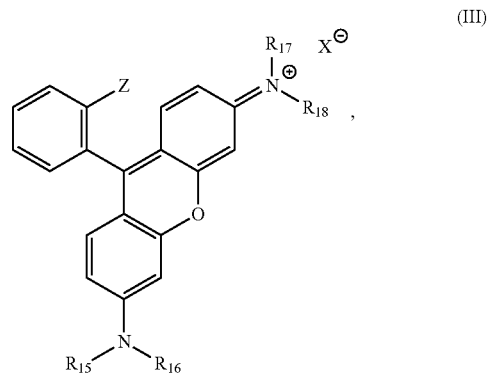

(III)

wherein $R_{15}$, $R_{16}$, $R_{17}$, and $R_{18}$ can be the same or different and are $C_nH_{2n+1}$, where n is an integer selected from the group consisting of 1, 2, 3, 4, 5, 6, 7 and 8;

X is an anion; and

Z is selected from the group consisting of: $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, and $CH_2(OCH_2CH_2)_rOVA$; and p is an integer selected from the group consisting of 1, 2, 3, 4, 5, 6, 7, 8, 9, 10, 11 and 12;

q is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and r is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

11. The method according to claim 9, wherein copolymerizing the probe for sensing glucose and the intra-reference probe, with 2-hydroxyethyl methacrylate, N-(6-aminohexyl) methacrylamide, and acrylamide forms poly(2-hydroxyethyl methacrylate), poly(N-(6-aminohexyl) methacrylamide), poly(acrylamide), poly(2-hydroxyethyl methacrylate)-co-polyacrylamide-co-poly(N-(6-aminohexyl) methacrylamide) and their composites with the polymerized probe for sensing glucose and the polymerized intra-reference probe.

12. A method of preparing an optical fluorescence dual sensor comprising the steps of:

(a) copolymerizing a probe for sensing oxygen and an intra-reference probe, with poly(2-hydroxyethyl methacrylate), polyacrylamide, and poly(2-hydroxyethyl methacrylate)-co-polyacrylamide onto a modified substrate; and (b) attaching or immobilizing a probe for sensing glucose onto the substrate;

wherein the probe for sensing glucose has formula I:

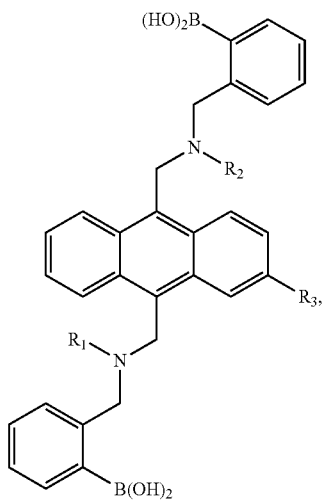
(I)

wherein $R_1$ and $R_2$ can be the same or different and are $C_nH_{2n+1}$, where n is an integer selected from the group consisting of 0, 1, 2, 3, 4, 5, 6, 7 and 8;

$R_3$ is selected from the group consisting of $(CH_2)_mC(O)OH$, $O(CH_2)_mC(O)OH$, $NH(CH_2)_mC(O)OH$, $(CH_2)_mC(O)OR_4$, $O(CH_2)_mC(O)OR_4$, $NH(CH_2)_mC(O)OR_4$, $(CH_2)_mC(O)NH(CH_2)_mNH-A$, $O(CH_2)_mC(O)NH(CH_2)_mNH-A$, $NH(CH_2)_mC(O)NH(CH_2)_mNH-A$, $(CH_2)_mC(O)O(CH_2)_mNH-A$, $O(CH_2)_mC(O)O(CH_2)_mNH-A$, $NH(CH_2)_mC(O)O(CH_2)_mNH-A$, $(CH_2)_mC(O)NH(CH_2)_mNH-M'A$, $O(CH_2)_mC(O)NH(CH_2)_mNH-M'A$, $NH(CH_2)_mC(O)NH(CH_2)_mNH-M'A$, $(CH_2)_mC(O)O(CH_2)_mNH-M'A$, $O(CH_2)_mC(O)O(CH_2)_mNH-M'A$, $NH(CH_2)_mC(O)O(CH_2)_mNH-M'A$, $(CH_2)_mC(O)NH(CH_2)_mNH-VA$, $O(CH_2)_mC(O)NH(CH_2)_mNH-VA$, $NH(CH_2)_mC(O)NH(CH_2)_mNH-VA$, $(CH_2)_mC(O)O(CH_2)_mNH-VA$, $O(CH_2)_mC(O)O(CH_2)_mNH-VA$, and $NH(CH_2)_mC(O)O(CH_2)_mNH-VA$;

m is an integer selected from the group of consisting of 0, 1, 2, 3, 4, 5, 6, 7, 8, 9, 10, 11 and 12;

$R_4$ is an activating group;

M'A is

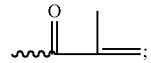

A is

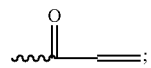

and

VA is

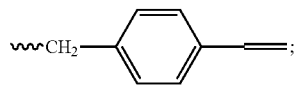

the probe for sensing oxygen has formula II:

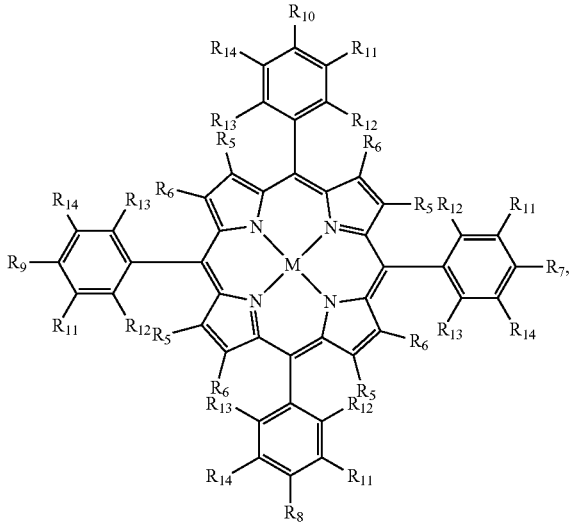
(II)

wherein M is selected from Pt or Pd;

$R_{11}$ and $R_{12}$ can be the same or different and are independently selected from the group consisting of H, F, Cl, Br, I, $CH_3$, $OCH_3$ and $OC_2H_5$;

$R_{13}$ and $R_{14}$ can be the same or different and are independently selected from the group consisting of H, F, Cl, Br, I, $CH_3$, $OCH_3$ and $OC_2H_5$;

$R_5$ and $R_6$ can be the same or different and are independently selected from the group consisting of H, F, Cl, Br, I, $CH_3$, $OCH_3$ and $OC_2H_5$;

$R_7$, $R_8$, $R_9$ and $R_{10}$ can be the same or different and are independently selected from the group consisting of $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, (OCH$_2$CH$_2$)$_q$OA, NH(CH$_2$CH$_2$O)$_q$A, (OCH$_2$CH$_2$)$_q$OVA, and NH(CH$_2$CH$_2$O)$_q$VA, where p is an integer selected from the group of consisting of 2, 3, 4, 5, 6, 7, 8, 9, 10, 11 and 12;

q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150;

and the intra-reference probe has formula III:

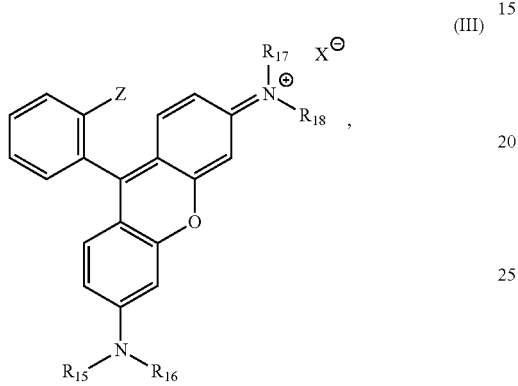

(III)

wherein $R_{15}$, $R_{16}$, $R_{17}$, and $R_{18}$ can be the same or different and are $C_nH_{2n+1}$, where n is an integer selected from the group consisting of 1, 2, 3, 4, 5, 6, 7 and 8;

X is an anion; and

Z is selected from the group consisting of: (CH$_2$)$_p$OH, O(CH$_2$)$_p$OH, NH(CH$_2$)$_p$OH, (CH$_2$)$_p$OM'A, O(CH$_2$)$_p$OM'A, NH(CH$_2$)$_p$OM'A, (CH$_2$)$_p$OA, O(CH$_2$)$_p$OA, NH(CH$_2$)$_p$OA, (CH$_2$)$_p$OVA, O(CH$_2$)$_p$OVA, NH(CH$_2$)$_p$OVA, (OCH$_2$CH$_2$)$_q$OH, NH(CH$_2$CH$_2$O)$_q$H, (OCH$_2$CH$_2$)$_q$OM'A, NH(CH$_2$CH$_2$O)$_q$M'A, (OCH$_2$CH$_2$)$_q$OA, NH(CH$_2$CH$_2$O)$_q$A, (OCH$_2$CH$_2$)$_q$OVA, NH(CH$_2$CH$_2$O)$_q$VA, CH$_2$(OCH$_2$CH$_2$)$_r$OA, CH$_2$(OCH$_2$CH$_2$)$_r$OM'A, and CH$_2$(OCH$_2$CH$_2$)$_r$OVA; and p is an integer selected from the group of consisting of 1, 2, 3, 4, 5, 6, 7, 8, 9, 10, 11 and 12;

q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and r is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

13. A method of preparing an optical fluorescence dual sensor comprising the step of:

copolymerizing a probe for sensing glucose, a probe for sensing oxygen and an intra-reference probe, with 2-hydroxyethyl methacrylate, N-(6-aminohexyl) methacrylamide, and acrylamide onto a modified substrate;

wherein the probe for sensing glucose has formula I:

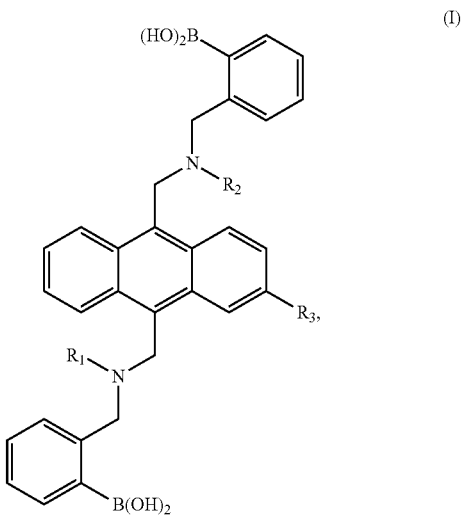

(I)

wherein $R_1$ and $R_2$ can be the same or different and are $C_nH_{2n+1}$, where n is an integer selected from the group consisting of 0, 1, 2, 3, 4, 5, 6, 7 and 8;

$R_3$ is selected from the group consisting of (CH$_2$)$_m$C(O)OH, O(CH$_2$)$_m$C(O)OH, NH(CH$_2$)$_m$C(O)OH, (CH$_2$)$_m$C(O)OR$_4$, O(CH$_2$)$_m$C(O)OR$_4$, NH(CH$_2$)$_m$C(O)OR$_4$, (CH$_2$)$_m$C(O)NH(CH$_2$)$_m$NH-A, O(CH$_2$)$_m$C(O)NH(CH$_2$)$_m$NH-A, NH(CH$_2$)$_m$C(O)NH(CH$_2$)$_m$NH-A, (CH$_2$)$_m$C(O)O(CH$_2$)$_m$NH-A, O(CH$_2$)$_m$C(O)O(CH$_2$)$_m$NH-A, NH(CH$_2$)$_m$C(O)O(CH$_2$)$_m$NH-A, (CH$_2$)$_m$C(O)NH(CH$_2$)$_m$NH-M'A, O(CH$_2$)$_m$C(O)NH(CH$_2$)$_m$NH-M'A, NH(CH$_2$)$_m$C(O)NH(CH$_2$)$_m$NH-M'A, (CH$_2$)$_m$C(O)O(CH$_2$)$_m$NH-M'A, O(CH$_2$)$_m$C(O)O(CH$_2$)$_m$NH-M'A, NH(CH$_2$)$_m$C(O)O(CH$_2$)$_m$NH-M'A, (CH$_2$)$_m$C(O)NH(CH$_2$)$_m$NH-VA, O(CH$_2$)$_m$C(O)NH(CH$_2$)$_m$NH-VA, NH(CH$_2$)$_m$C(O)NH(CH$_2$)$_m$NH-VA, (CH$_2$)$_m$C(O)O(CH$_2$)$_m$NH-VA, O(CH$_2$)$_m$C(O)O(CH$_2$)$_m$NH-VA, and NH(CH$_2$)$_m$C(O)O(CH$_2$)$_m$NH-VA;

m is an integer selected from the group consisting of 0, 1, 2, 3, 4, 5, 6, 7, 8, 9, 10, 11 and 12;

$R_4$ is an activating group;

M'A is

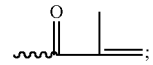

A is

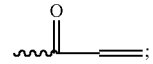

and

VA is

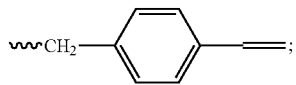

the probe for sensing oxygen has formula II:

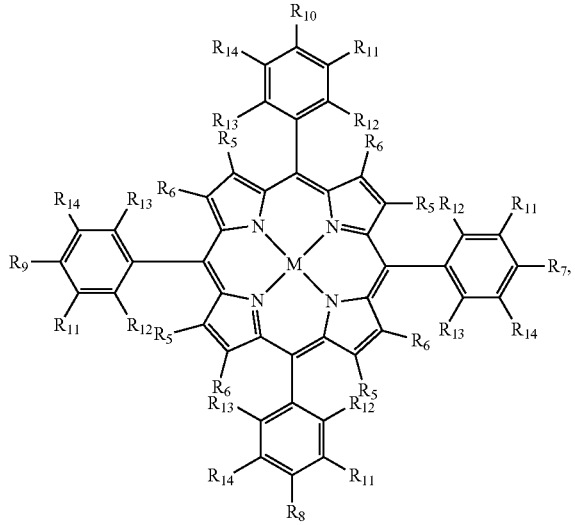

wherein M is selected from Pt or Pd;

$R_{11}$ and $R_{12}$ can be the same or different and are independently selected from the group consisting of H, F, Cl, Br, I, $CH_3$, $OCH_3$ and $OC_2H_5$;

$R_{13}$ and $R_{14}$ can be the same or different and are independently selected from the group consisting of H, F, Cl, Br, I, $CH_3$, $OCH_3$ and $OC_2H_5$;

$R_5$ and $R_6$ can be the same or different and are independently selected from the group consisting of H, F, Cl, Br, I, $CH_3$, $OCH_3$ and $OC_2H_5$;

$R_7$, $R_8$, $R_9$ and $R_{10}$ can be the same or different and are independently selected from the group consisting of $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, and $NH(CH_2CH_2O)_qVA$, where p is an integer selected from the group consisting of 2, 3, 4, 5, 6, 7, 8, 9, 10, 11 and 12;

q is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150;

and the intra-reference probe has formula III:

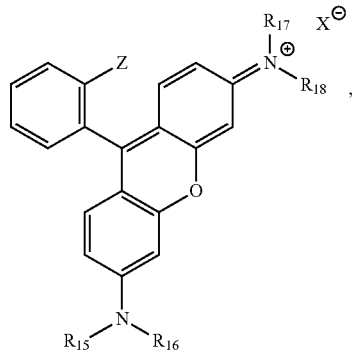

wherein $R_{15}$, $R_{16}$, $R_{17}$, and $R_{18}$ can be the same or different and are $C_nH_{2n+1}$, where n is an integer selected from the group consisting of 1, 2, 3, 4, 5, 6, 7 and 8;

X is an anion; and

Z is selected from the group consisting of: $(CH_2)_pOH$, $O(CH_2)_pOH$, $NH(CH_2)_pOH$, $(CH_2)_pOM'A$, $(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, $CH_2(OCH_2CH_2)_rOA$, $CH_2(OCH_2CH_2)_rOM'A$, and $CH_2(OCH_2CH_2)_rOVA$; and p is an integer selected from the group of consisting of 1, 2, 3, 4, 5, 6, 7, 8, 9, 10, 11 and 12;

q is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150; and r is an integer selected from the group consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

14. The method according to claim 13, wherein copolymerizing the probe for sensing glucose, the probe for sensing oxygen and the intra-reference probe, with 2-hydroxyethyl methacrylate, N-(6-aminohexyl) methacrylamide, and acrylamide forms poly(2-hydroxyethyl methacrylate), poly(N-(6-aminohexyl) methacrylamide), poly(acrylamide), poly(2-hydroxyethyl methacrylate)-co-polyacrylamide-co-poly(N-(6-aminohexyl) methacrylamide) and their composites with the polymerized probe for sensing glucose, the polymerized probe for sensing oxygen and the polymerized intra-reference probe.

15. The method according to claim 8 or 12, wherein the probe for sensing glucose is:

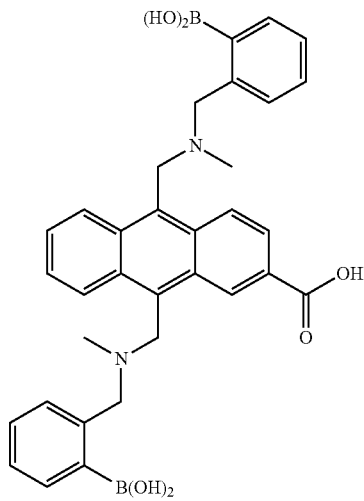 [SMILES: CN(Cc1ccccc1B(O)O)Cc1c2ccccc2c(CN(C)Cc2ccccc2B(O)O)c2cc(C(=O)O)ccc12]

or an activated ester thereof.

16. The method according to claim 12 or 13, wherein the probe for sensing oxygen is:

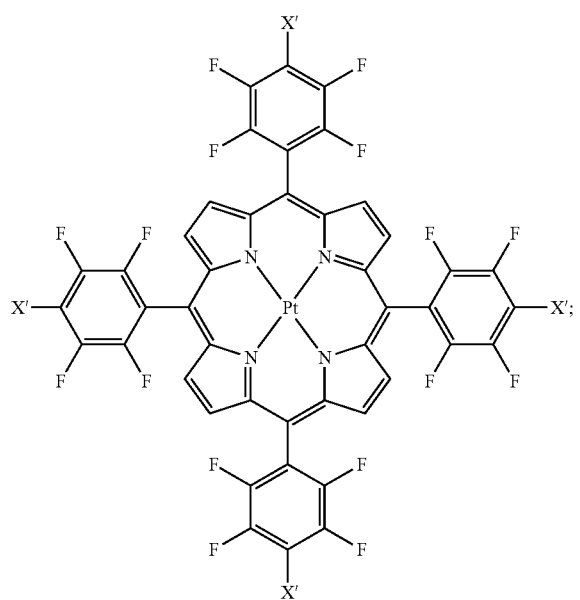

wherein X' is

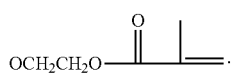

17. The method according to any one of claims 8 to 13, wherein the intra-reference probe is:

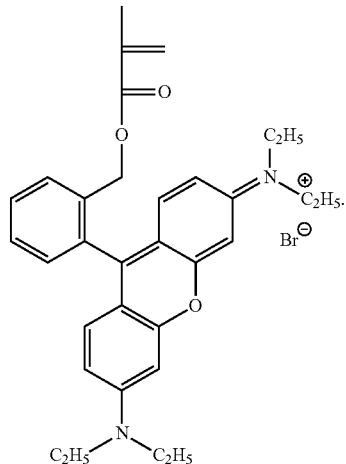

18. A method of determining the concentration of glucose in a sample comprising:
   (a) exposing the sample to an optical fluorescence sensor according to claim 1 or an optical fluorescence dual sensor according to claim 4;
   (b) irradiating the sensor at a first wavelength to produce a glucose indicator emission signal at a second wavelength and an intra-reference emission signal at a third wavelength;
   (c) measuring the glucose indicator emission signal at the second wavelength;
   (d) measuring the intra-reference emission signal at the third emission wavelength; and
   (e) ratiometrically determining the concentration of glucose in the sample.

19. The method according to claim 18, wherein more than one sample is used.

20. The method according to claim 18, wherein the sample comprises a bodily fluid.

21. The method according to claim 20, wherein the bodily fluid comprises blood.

22. The method according to claim 18, wherein the sample is obtained from a cell culture or a subject.

23. The method according to claim 18, wherein the sample is selected from the group consisting of live single cells, live several cells, live cell clusters, and live tissue.

24. A method of determining the concentration of oxygen in a sample comprising:
   (a) exposing the sample to an optical fluorescence dual sensor according to claim 4;
   (b) irradiating the sensor at a first wavelength to produce an oxygen indicator emission signal at a second wavelength and an intra-reference emission signal at a third wavelength;
   (c) measuring the oxygen indicator emission signal at the second wavelength;
   (d) measuring the intra-reference emission signal at the third emission wavelength; and
   (e) ratiometrically determining the oxygen concentration in the sample.

25. A method of simultaneously determining the concentration of glucose and the concentration of oxygen in a sample comprising (a) exposing the sample to an optical fluorescence dual sensor according to claim 4;
(b) irradiating the sensor at a first wavelength to produce a glucose indicator emission signal at a second wavelength, an oxygen indicator emission signal at a third wavelength and an intra-reference emission signal at a fourth wavelength;
(c) measuring the glucose indicator emission signal at the second wavelength;
(d) measuring the oxygen indicator emission signal at the third wavelength;
(e) measuring the intra-reference emission signal at the fourth wavelength;
(f) ratiometrically determining the concentration of glucose in the sample using the measurements obtained in steps (c) and (e); and
(g) ratiometrically determining the oxygen concentration in the sample using the measurements obtained in steps (d) and (e).

* * * * *